(12) United States Patent
Chiarello et al.

(10) Patent No.: US 7,317,533 B2
(45) Date of Patent: Jan. 8, 2008

(54) METAL ION CONCENTRATION ANALYSIS FOR LIQUIDS

(75) Inventors: Ronald P. Chiarello, Los Gatos, CA (US); Eric Boyd, San Jose, CA (US); Duncan A. McPhee, Campbell, CA (US)

(73) Assignee: Jetalon Solutions, Inc., Los Gatos, CA (US)

( * ) Notice: Subject to any disclaimer, the term of this patent is extended or adjusted under 35 U.S.C. 154(b) by 528 days.

(21) Appl. No.: 11/036,962

(22) Filed: Jan. 14, 2005

(65) Prior Publication Data
US 2006/0158653 A1    Jul. 20, 2006

(51) Int. Cl.
*G01N 21/55* (2006.01)
(52) U.S. Cl. ...................... 356/445; 356/440
(58) Field of Classification Search ........ 356/445–448, 356/432–440
See application file for complete search history.

(56) References Cited

U.S. PATENT DOCUMENTS

| | | | |
|---|---|---|---|
| 3,751,672 A | 8/1973 | Michel et al. | |
| 4,704,029 A | 11/1987 | Van Heuvelen | |
| 4,778,270 A | 10/1988 | Kinney et al. | |
| 5,364,510 A | 11/1994 | Carpio | |
| 5,442,435 A | 8/1995 | Cooper et al. | |
| 5,565,978 A | 10/1996 | Okubo et al. | |
| 5,617,201 A | 4/1997 | Kahre | |
| 5,898,503 A | 4/1999 | Keller et al. | |
| 5,912,456 A | 6/1999 | Melendez et al. | |
| 5,922,285 A | 7/1999 | Melendez et al. | |
| 5,946,083 A | 8/1999 | Melendez et al. | |
| 6,024,923 A | 2/2000 | Melendez et al. | |
| 6,045,756 A | 4/2000 | Carr et al. | |
| 6,097,479 A | 8/2000 | Melendez et al. | |

(Continued)

FOREIGN PATENT DOCUMENTS

JP        401170838 A      7/1989

OTHER PUBLICATIONS

Chinowsky, T. M. et al., Perfomance of the Spreeta 2000 Integrated Surface Plasmon Resonance Affinity Sensor, Sensors and Actuators B 6954, pp. 1-9, 2003.

(Continued)

*Primary Examiner*—Gregory J. Toatley, Jr.
*Assistant Examiner*—Tri Ton
(74) *Attorney, Agent, or Firm*—Steven D. Hemminger; Akin, Gump, Strauss, Hauer & Feld LLP

(57) ABSTRACT

An apparatus utilizes miniaturized surface plasmon resonance (SPR) and ion-selective self-assembled monolayer (SAM) and hydrogel chemistry to measure metal ion concentrations in liquids. The SPR optical system is packaged in a compact and cost-effective form factor. An electronic circuit drives the optical system. The SPR system utilizes an optical window that is coated with the SAM layer or hydrogel material. The SAM layer and hydrogel materials are highly selective to a specific metal ion of interest. The miniaturized SPR sensor is situated in an optical-fluidic cell or an optical-fluidic manifold with the SAM layer or hydrogel material in contact with the liquid. Metal ions selectively attach to the SAM layer or hydrogel material, thereby affecting the SPR signal. Changes in the SPR signal are used to accurately determine the metal ion concentration in the liquid. The liquids may be either static or dynamic.

62 Claims, 19 Drawing Sheets

U.S. PATENT DOCUMENTS

| | | |
|---|---|---|
| 6,111,248 A | 8/2000 | Melendez et al. |
| 6,111,652 A | 8/2000 | Melendez et al. |
| 6,118,520 A | 9/2000 | Harner |
| 6,183,696 B1 | 2/2001 | Elkind et al. |
| 6,191,847 B1 | 2/2001 | Melendez et al. |
| 6,239,255 B1 | 5/2001 | Furlong et al. |
| 6,267,641 B1 | 7/2001 | Vanell et al. |
| 6,326,612 B1 | 12/2001 | Elkind et al. |
| 6,374,845 B1 | 4/2002 | Melendez et al. |
| 6,386,894 B2 | 5/2002 | Carr |
| 6,401,974 B1 | 6/2002 | Elkind |
| 6,415,235 B1 | 7/2002 | Bartholomew et al. |
| 6,549,276 B1 | 4/2003 | Longtin |
| 6,574,575 B2 | 6/2003 | Deng et al. |
| 6,594,018 B1 | 7/2003 | Bartholomew |
| 6,885,455 B2 | 4/2005 | Bartholomew et al. |
| 7,064,816 B2 | 6/2006 | Langenbacher et al. |
| 7,144,153 B2 | 12/2006 | Sato |
| 7,184,639 B2 * | 2/2007 | Hamada ................. 385/129 |
| 2005/0046853 A1 | 3/2005 | Sato |
| 2005/0110989 A1 | 5/2005 | Schermer et al. |
| 2005/0179901 A1 | 8/2005 | Ostlin et al. |
| 2006/0094941 A1 | 5/2006 | Cho |
| 2006/0158653 A1 | 7/2006 | Chiarello et al. |

OTHER PUBLICATIONS

Geake, J. E et al., A Linear Differentiating Refractometer, Meas. Sci. Technol. 5 pp. 531-539, Printed in the UK, 1994.

Geake, J.E. et al., The Huygens SSP Refractometer, Proceedings Symposium of Titan, Apr. 1992.

Lorenz, R. D., Raindrops of Titan, Adv. Space Res., vol. 15, No. 3, pp. (3)317-(3)320, 1995.

Meeten G. H. et al., Refractive Index Measurement of Absorbing and Turbid Fluids by Reflection near the Critical Angle, Meas. Sci. Technol. 6, pp. 214-221, Printed in the UK, 1995.

* cited by examiner

Liquid Flow Path

US 7,317,533 B2

METAL ION CONCENTRATION ANALYSIS FOR LIQUIDS

BACKGROUND OF THE INVENTION

1. Field of the Invention

The present invention relates to the field of analytical chemical instrumentation utilizing optical sensors and in particular to integrated optical-chemical analytical instrumentation used in the fields of chemical, biochemical, biological or biomedical analysis, process control, pollution detection and control, and other similar areas.

2. Discussion of the Related Art

Referring to FIG. 1, a prior art optical sensor 100 is shown. The optical sensor 100 utilizes surface plasmon resonance (SPR). The electro-optic components of the optical sensor 100, including light emitting diode 120, photodetector array 110, and temperature sensor 125, may be encapsulated within a trapezoidal-shaped optical housing 150 and coupled to an interior surface 161 of a substrate 160. A plurality of conductive leads 165 are coupled to an exterior surface 162 of the substrate 160. An optical window 140 made from glass is attached to the optical housing 150 to form part of sensing surface 145, which includes a gold (Au), silver (Ag) or copper (Cu) metal thin film 145 deposited onto a surface of the glass optical window 140. The layer 145 is preferably planar although other configurations, such as convex or concave configurations, or featured with steps, periodic or non-periodic, can also be utilized. This layer 145 may comprise a Au film approximately 175 Å thick. The thickness of the Au layer may vary from about 175 to about 600 Å and still permit SPR to occur. The specific film thickness is determined by the frequency of the radiation for the light source 120 and the properties of the conductive material used for layer 145.

Optical housing 150 has an optical geometry such that light from a light emitting diode (LED), solid state laser or other appropriate light source 120 will reflect from sensing surface 145 to mirrored surface and then strike photodetector 110. Light source 120 may comprise a LED, laser diode, light filament, halogen lamp, or other suitable source of electromagnetic radiation. In one embodiment of the prior art, a plurality of light sources that emit light of different wavelengths may be used. The photodetector 110 is multi-channeled and may be linear or two-dimensional. Other configurations of optical housing 150 may be employed consistent with optical sensor 100. For example, light from LED 120 may reflect from mirrored surface to sensing surface 145 and then strike a photodetector 110.

Optical housing 150 is made of a light transmissive material in which light 127 from light source 120 travels. Suitable materials include glass, plastic or hardened epoxy, although other materials may be used that preferably will not damage the encapsulated components. In particular, an epoxy marketed under the trademark Epocast.RTM. 2013 Parts A/B by Furane Products Company has been found useful, especially for radiation sources in the infrared range. Other usable materials include Emerson & Cumming, Stycast 1269A Parts A/B, Tracon Trabond F114, Dexter Hysol OS1000, Norland 61 and 63, Dexter Hysol MG18, and Nitto 8510-1100.

Optical housing 150 is coupled to the substrate 160 to form an encapsulated self-contained sensor 100. The substrate 160 may be made of a dark, light-absorbing material, such as a hard resin or epoxy. However, the material of substrate 160 depends primarily on the radiation properties of light source 120. Also, substrate 160 may be coated with a dark layer of light-absorbing material such as polyurethane epoxy or a thin resin layer among others.

Temperature sensor 125 may also be embedded within housing 150 and coupled to interior surface 161 of substrate 160. It is desirable that temperature sensor 125 be disposed as close to the sensing surface 145 as is practical. A polarizer 121 may be used to produce transverse magnetic polarized light (the electric field polarized in a plane of incidence being the sensing surface 145) from the light source 120. A filter (not shown) may also be used to screen out radiation at wavelengths other than wavelengths produced by light source 120. This filter may overlay photodetector 110 and serves to pass radiation at the wavelengths produced by light source 120 to photodetector 110. As such, the filter eliminates unwanted noise caused by other radiation sources in proximity to the sensor 100. One suitable filter is a plastic filter material marketed by Polaroid Corporation known as XR-84. This material is especially suitable for passing infrared radiation and blocking visible radiation.

An alternative to utilizing a filter is to utilize a plastic or epoxy material for the housing 150 which is transparent to wavelengths produced by the light source 120 and opaque to frequencies outside the desired frequency range of interest for a given sensor/sample combination. Likewise, an absorbing die can be enclosed in the housing 150 to achieve the same function.

Those of skill in the art will recognize that the elements of sensor 100 can be relocated, or rearranged about the sensor substrate 160 while retaining equivalence in function according to the invention. For example, mirrored surfaces utilized for reflecting the light rays could take on other configurations and locations within the sensor 100 so long as the light strikes the sensing surface 145 and the intensity of the radiation reflected therefrom is measured as a function of the angle of the radiation striking the sensing surface 145. Photodetector array 110 receives the light incident over a broad range of angles and yields a voltage output for each light cell where sufficient light is sensed. The output of each cell can be carried on interface 165, as individual binary signals of each photo cell, to an external system or component (not shown), such as a DSP, PC104-based microprocessor, hand-held meter, calculator, printer, logic analyzer, oscilloscope, or other similar system.

Referring to FIG. 2, the well established optical geometry for SPR is illustrated. The angle (θ) at which SPR occurs is highly dependant on the refractive index of the material in contact with the thin metal film 145 deposited on the dielectric 140. As is known in the art, when radiation strikes a thin conductive film at the interface of an insulator, the intensity of reflection thereof is a function of the angle of incidence of the radiation onto the film and the refractive index of the material in contact with the other side of the film. Hence, by determining the angle at which minimum reflectance occurs, it is possible to determine the index of refraction of the material on the side of the film opposite the side the radiation is reflected from. For a given wavelength of the incident light, resonance occurs at a specific angle of incidence that is dependent on the index of refraction of material in contact with the thin metal film. Therefore, changes in the index of refraction of the material in contact with the thin metal film result in changes in the SPR angle.

Miniaturized SPR sensors are becoming available for use in some biochemical applications, but their overall usefulness in other applications is limited. Specifically, the direct detection of metal ions in liquids by a miniaturized, cost-effective, accurate sensor is not known to exist. Currently, for most applications, highly accurate, reliable metal ion concentration analysis is restricted to laboratory scale measurements made ex situ and off site from grab samples. Metal ion concentration systems that may be used "in the field," are expensive, have slow response times, and are large and bulky—essentially expensive and inconvenient. What is needed is a miniaturized, cost-effective, accurate sensor for use in situ for the direct detection of metal ions in liquids.

SUMMARY OF THE INVENTION

The present invention marks a step forward in metal ion concentration analysis for liquid chemicals, in that it is a real-time, cost-effective system packaged in a compact form factor that is conveniently integrated into many applications. The present invention, by combining a miniaturized SPR optical sensor with two-dimensional and mesoscopic scale chemistry directly addresses the limitations of current metal ion analysis systems for liquids. The current invention integrates SPR with novel self-assembled monolayer (SAM) or hydrogel chemistries for use as a metal ion concentration sensor. Furthermore, such a metal ion concentration sensor is robust and conveniently integrated for manufacturing, field, and home applications.

Embodiments of the present invention provide for an optical sensor that integrates SPR with self-assembled monolayer (SAM) or hydrogel chemistries for use as a metal ion concentration analysis sensor. SPR is an optical surface phenomenon that is employed in the fields of chemical, biochemical, biological or biomedical analysis. SAMs may be defined as a two-dimensional film, bonded at an interface via a process whereby individual components of the layer spontaneously organize, typically from a solution or gas phase until a stable structure of minimum energy is reached, into more complex structures. Components in self-assembled structures find their appropriate location based on their structural and chemical properties and on their reaction with the chemical and structural properties of the substrate. Adsorption of metal ions from liquids has been demonstrated with high selectivity using SAM and hydrogel materials.

DETAILED DESCRIPTION

According to embodiments of the present invention, a metal ion concentration analysis sensor and system for liquids is described. In the preferred embodiment, the analysis sensor is used in situ and at a point-of-use. The analysis sensor and system are applicable to many metal ion analysis applications. The sensor analyzes metal ion concentration for acids, bases, aqueous-based liquids, solvents, and ultra-high purity, caustic and corrosive liquids. The invention is useful in manufacturing facilities, water treatment and water recycling/reclaim systems (both industrial and municipal), medical applications, and ground and surface water sources. In various embodiments, the invention can be integrated into liquid recycling systems, municipal water treatment facilities and into small scale at home water treatment systems. The present invention may be connected to a flowing liquid via input and output lines, immersed into a static reservoir or injected with a sample of a liquid. The analysis system provides concentration information in real-time (0.001-10 seconds), has a compact form factor (<2"×2"×1") and a concentration sensitivity well below parts per million (ppm) levels of metal ions. The analysis system has capabilities as both a monitoring system and as a closed-loop control system for interface with actuators for liquid chemicals such as pumping systems, diverting systems, variable flow valves, etc.

Figure 1:
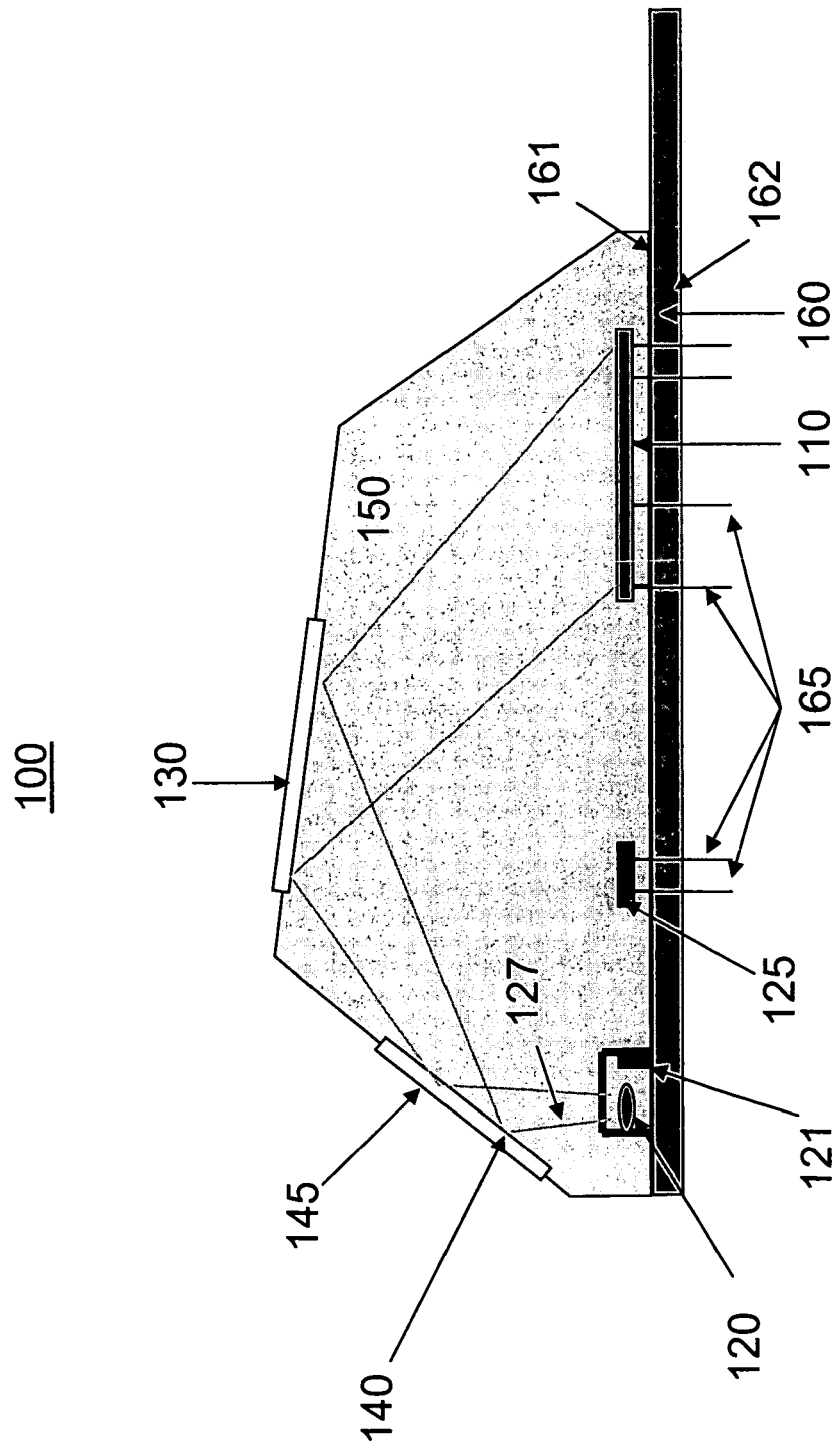
FIG. 1 illustrates a prior art miniaturized optical sensor.
Figure 2:
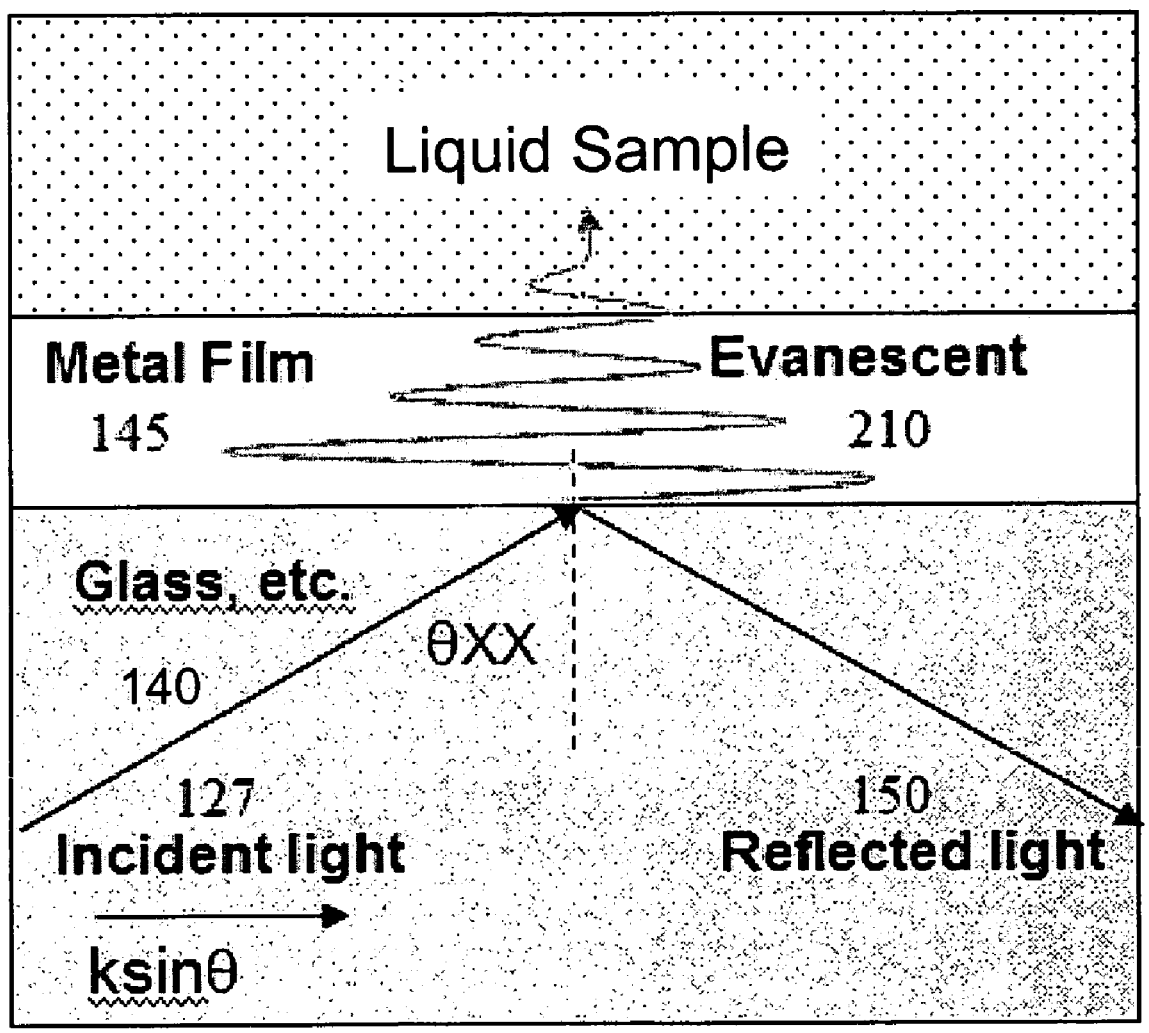
FIG. 2 illustrates prior art surface plasmon resonance geometry and phenomenon.
Figure 3:
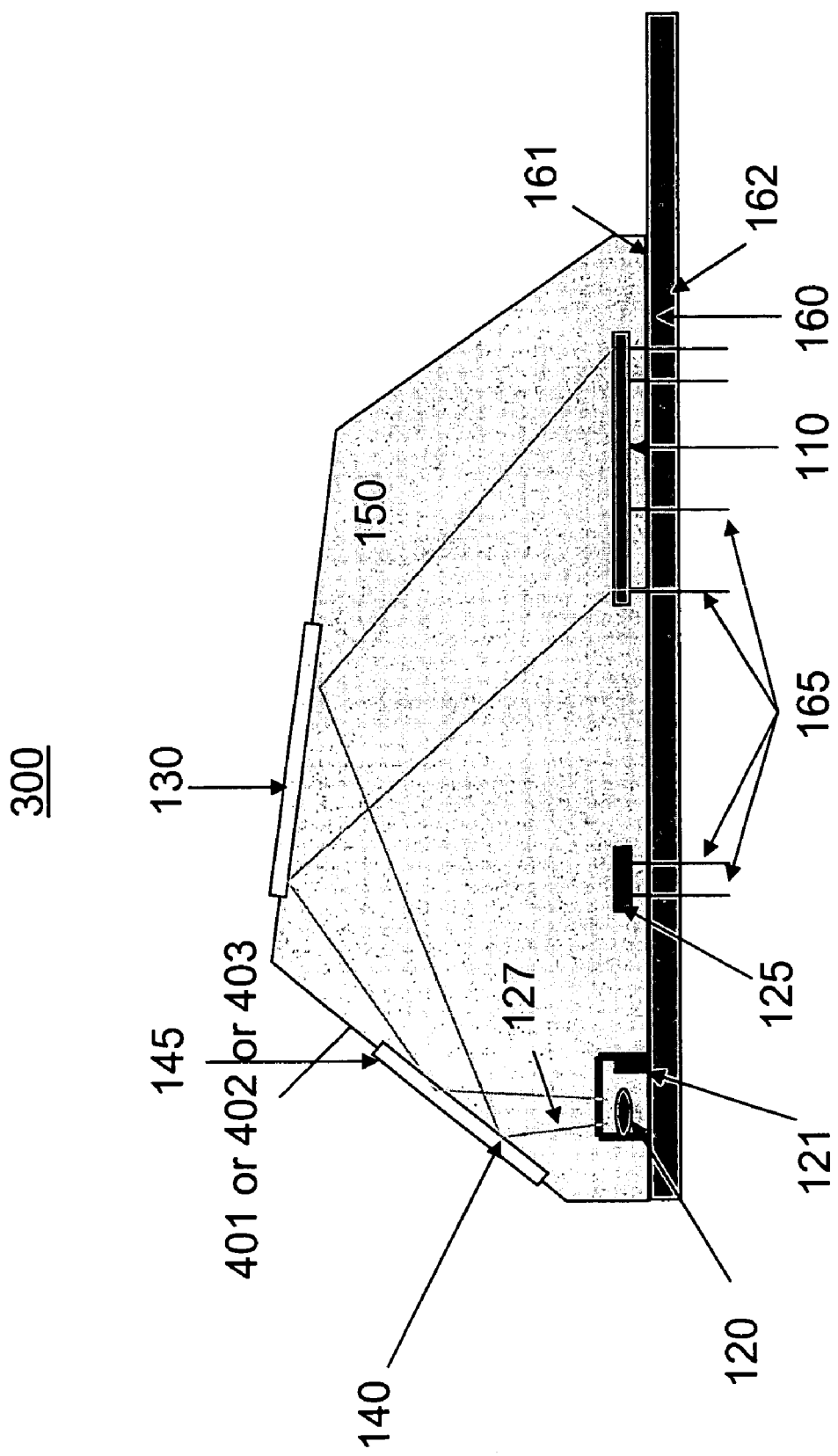
FIG. 3 illustrates a miniaturized optical system including two-dimensional and mesoscopic chemistries attached to an optical window according to an embodiment of the present invention.

Referring to FIG. 3, the principle of operation of the optical sensor 300 of the present invention combines a miniaturized, fully integrated surface plasmon resonance (SPR) optical sensor with self-assembled monolayers (SAMs) or hydrogel technologies 401-403 (see FIGS. 4a-c) to form a compact, real-time, cost-effective metal ion analysis sensor for liquids.

The miniaturized and integrated optical sensor 300 includes a light source 120, a polarizer 121 (optional), a temperature sensor 125, a multi-channel photon detector 110, a mirror 130, and an optical window made of a dielectric material, for example, sapphire, quartz, glass, or a similar appropriate dielectric material 140, which is coated with a thin metal conducting film of high free electron density such as Au, Ag, or Cu 145.

Figure 4A:
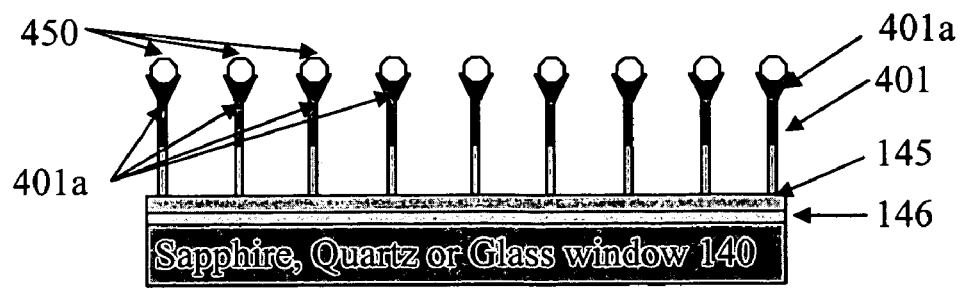
FIG. 4a illustrates a self-assembled monolayer (SAM) according to an embodiment of the present invention.
Figure 4B:
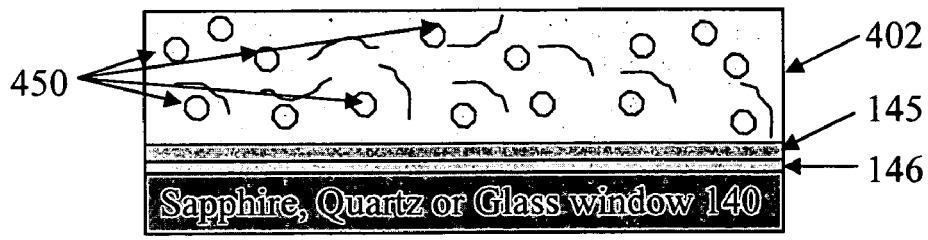
FIG. 4b illustrates a hydrogel layer according to an embodiment of the present invention.
Figure 4C:
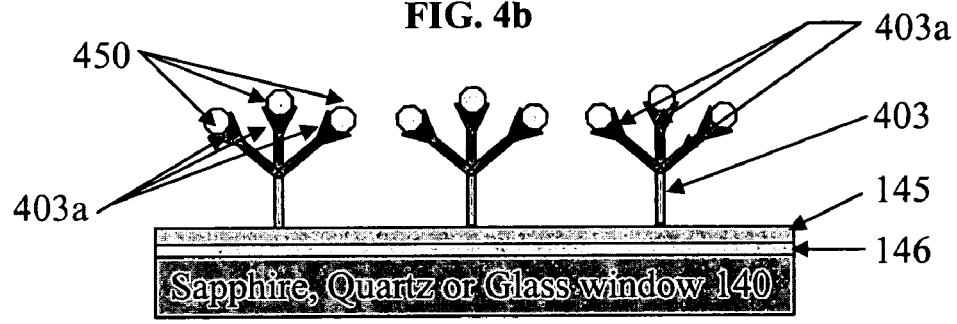
FIG. 4c illustrates a self-assembled monolayer+ (SAM+) according to an embodiment of the present invention.

Referring to FIGS. 4a-c, the optical window 140 is coated with the following materials selected and engineered for analysis of metal ions in liquids: A thin ($\leq 100$ Å) titanium (Ti) or chromium (Cr) layer 146, used to aid in the adhesion, flatness and two-dimensional crystalline of any subsequent layer. A thin metal film 145 ($\leq 500$ Å) of a high free electron density metal (such as gold (Au), silver (Ag), or copper (Cu), etc.) is deposited onto the Ti (or Cr) adhesion layer 146.

Referring to FIG. 4a according to an embodiment of the present invention, a self-assembled monolayer (SAM) 401 is reacted onto the thin metal film 145 surface in a densely packed, two-dimensionally ordered (in the plane of the surface) structure. Examples of SAM materials include isalkanethiol, n-octadecanethiol, mercaptopropionic acid, L-cysteine, and mercaptohexadecanoic acid. Other SAM materials may be used.

SAMs are defined as a two-dimensional film, bonded at an interface via a process whereby individual components of the layer spontaneously organize, typically from a solution or gas phase until a stable structure of minimum energy is reached, into more complex structures. Components in self-assembled structures find their appropriate location based on their structural and chemical properties and on their reaction with the chemical and structural properties of the substrate.

A head group 401a of the SAM 401 material can interact with a metal ion 450 of interest by chemisorption (chemical bond, covalent bond), physisorption (electrostatic without chemical bond), or geometrical/spatial confinement. It is possible to engineer a specific type of interaction by changing the SAM headgroup 401a. A plurality of head groups may form a molecular adhesion layer. It is also possible to combine multiple types of interactions in the same SAM material, for example, chemisorption or physisorption with spatial confinement.

Referring to FIG. 4b according to a second embodiment of the present invention, the SAM material is replaced by an electric hydrogel 402 material. A hydrogel 402 is a polymeric material that swells when exposed to water. By controlling a hydrogel's chemical makeup, the degree of swelling can be made sensitive to environmental conditions such as temperature, pH, and analyte (a substance undergoing analysis) concentration. A change in volume of the hydrogel can be measured in a variety of physical and optical ways and thus provides the basic element of a sensor. Metal ions 450 can bond to the hydrogel 402 surface, or internally throughout the hydrogel 402. Metal ion bonding to the hydrogel can be covalent, electrostatic or geometrical/spatial.

Hydrogel 402 materials can adsorb metal ions 450 from liquids with high specificity. Hydrogels 402 are mesoscopic (between 2 and 3 dimensions) materials that a) can be chosen to only attract specific metal ions 450 of interest, b) have high selectivity and c) have a larger surface area than SAM 401 materials and therefore an increased number of binding sites for metal ions 450 under analysis. Because of this feature, hydrogel 402 materials may provide increased sensitivity and dynamic range by attracting a greater number of metal ions 450 than may be possible via use of SAM 401 materials.

Referring to FIG. 4c according to a third embodiment of the present invention, a SAM has a plurality of metal ion head group/binding sites 403a. This material may be referred to as a SAM+.

The SAM 401, hydrogel materials 402, and SAM+403 materials are engineered/selected for high-selectivity of metal ions in liquids. Bonding of the metal ion 450 to the SAM 401, hydrogel 402, and SAM+403 materials may occur via the following mechanisms; physisorption (van der Waals, Coulombic, electrostatic interactions), chemisorption (chemical bond), and geometrical or spatial bonding, depending on the material.

SAM+403 and hydrogel 402 materials afford an increased number of metal ion binding sites as compared with SAM 401 materials. In this way, more metal ions can be adsorbed at a surface and therefore increase the sensitivity and dynamic range of the metal ion analysis sensor.

In various embodiments of the present invention the SAM 401, hydrogel 402 and SAM+403 materials are chosen to: 1) selectively bind to metal ions of interest, while rejecting other species in the liquid; 2) have a tunable activation energy to selectively bind to metal ions of interest depending on the concentration level of the metal ion of interest in the liquid; 3) have the capability to simultaneously analyze several metal ions of interest, by for example, patterning and coating the Au surface 145 of window 140 of a single optical sensor 300 with up to three unique SAM 401, hydrogel 402 or SAM+403 materials, one for each of three optical channels; 4) simultaneously analyze several metal ions of interest by using several optical sensor heads, each individual window 140 patterned and coated with a specific metal-ion selective SAM 401, hydrogel 402 and/or SAM+403 material. It may also be possible to mix and match these embodiments into distinct combinations of patterned and unpatterned, SAM 401, hydrogel 402, and SAM+403 coated sensors 300 arrays (see for example FIG. 6a-e).

Referring to FIG. 3 and FIGS. 4a-c, the effect of combining a miniaturized, fully integrated SPR optical sensor with SAM 401, hydrogel 402 and SAM+403 chemistries is described. The precise angle of incidence at which SPR occurs is determined by a number of factors, the principal determinant being the refractive index close to the backside of the metal film 145. When metal ions bind from the liquid to the SAM 401, hydrogel 402, or SAM+403 materials, the local refractive index changes. This leads to a change in SPR angle, which can be monitored in real-time by measuring and analyzing changes in the intensity of the reflected light. The size of the change in the SPR signal's angular position is related to the number of metal ions bound to the SAM 401, hydrogel 402 or SAM+403 material. Since the SPR signal strongly depends on binding at the SAM 401, hydrogel 402, or SAM+403 material, it may be possible to analyze for metal ions constituents in complex liquids. In some instances, depending on the complexity of the liquid under analysis, it may be necessary to perform differential SPR measurements. In such cases, the background contribution of the bulk liquid to the SPR signal is measured and algebraically subtracted from the total SPR signal. This may be described mathematically in the equation below:

$$SPRS_{Surface+Bulk} - SPR_{Bulk} = SPR_{Surface}$$

Additionally, the SPR signal is also affected by the presence of the SAM 401, hydrogel 402, or SAM+403 material itself. A further refinement of the SPR signal due only to the presence of metal ions at the sensor surface is:

$$SPR_{SAM+metalion} - SPR_{SAM} = SPR_{metalion}$$

Similarly for embodiments using hydrogel chemistry:

$$SPR_{Hydrogel+metalion} - SPR_{Hydrogel} = SPR_{metalion}$$

Similarly for embodiments using the SAM+material:

$$SPR_{SAM++metalion} - SPR_{SAM} = SPR_{metalion}$$

For the current invention, SPR signal analysis and refinement of this type may lead to increased sensitivity and dynamic range of the metal ion analysis sensor.

In an alternative embodiment of the present invention, the index of refraction (concentration) of the liquid may be determined by using a prior art SPR optical sensor 100 and the concentration of metal ions in the liquid may be determined using a SPR/SAM optical sensor 300 or a SPR/hydrogel optical sensor 300. Both measurements may be made simultaneously.

The specificity of the optical sensor 300 may be determined by the sensing surface, i.e., the coating on the optical window 140 of the optical sensor 300 (see FIG. 3 and FIGS. 4*a-c*). For example, the coating on the Au surface 145 of window 140 of optical sensor 300 may include SAM 401, hydrogel 402, or SAM+403 materials, or any combination of the three. An optical sensor 300 that utilizes SPR with a specific SAM layer or hydrogel layer measures the concentration of a particular metal ion. The SPR optical sensor 100 without a SAM layer measures a critical angle to determine the index of refraction (concentration) of the liquid. Both types, optical sensor 100 and optical sensor 300, may be included in one optical system.

Figure 4D:
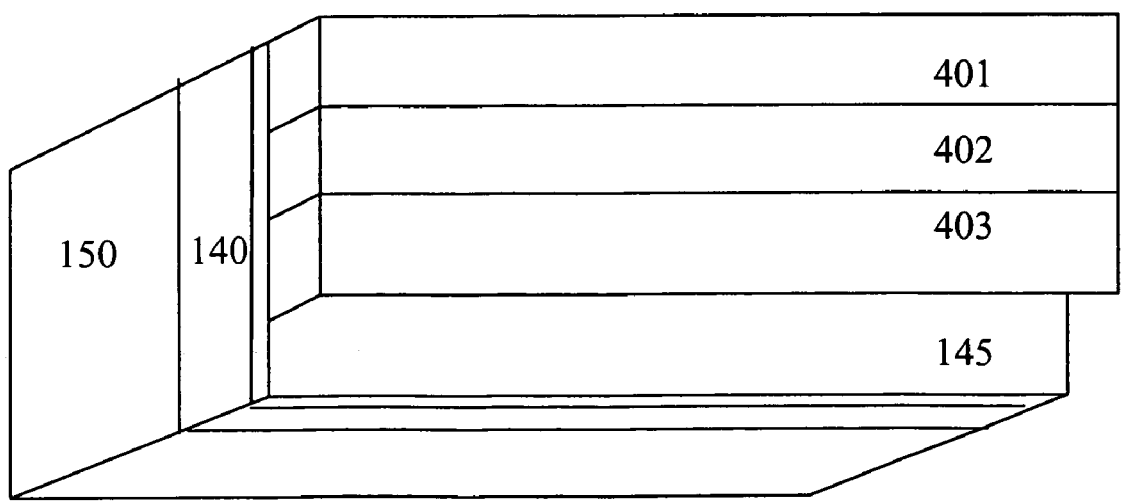
FIG. 4d illustrates a multi-channel optical sensor according to an embodiment of the present invention.

Alternatively, a multi-channel optical sensor 300 may be used (see FIG. 4*d*). The optical window 140 of the single multi-channel optical sensor 300 is patterned and coated with materials such that a section of the window 140 has no SAM layer deposited on top of metal surface 145 and measures the refractive index of the liquid, while a separate section of the window surface 140 is patterned and coated with a SAM 401 layer, a hydrogel layer 402, or a SAM+403 layer to measure a metal ion concentration in the liquid.

In both cases, whether using a single multi-channel optical sensor or two optical sensors, the concentration of the liquid (background signal) may be subtracted from the signal due to the concentration of the metal ions of interest. This alternative background signal reduction method also improves the resolution and the lower-level detection limit for metal ion concentration analysis.

Figure 5:
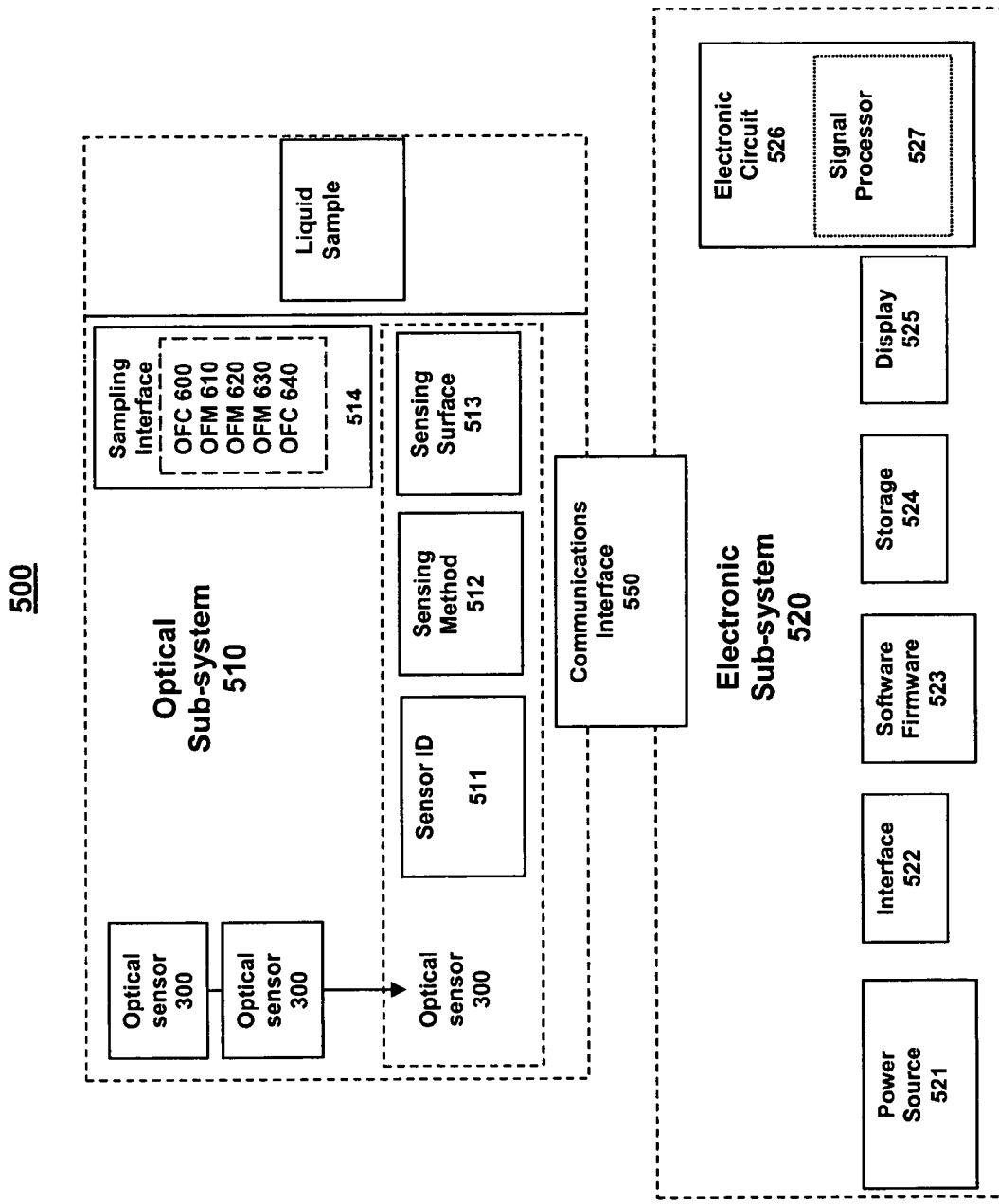
FIG. 5 illustrates a detailed block diagram of a metal ion analysis system according to an embodiment of the present invention.

Referring to FIG. 5, an analysis system 500 according to embodiments of the present invention includes an optical sub-system 510 including at least one optical sensor 300, an optical-fluidic cell (OFC) 600, 640 (see FIGS. 6*a* and 6*e*) or optical-fluidic manifold (OFM) 610-630 630 (see FIGS. 6*b-d*), and an electronic sub-system 520 including an electronic circuit 526.

The optical sub-system 510 of the analysis system 500 may include a plurality of optical sensors 300 each having a sensor ID 511 such as a barcode, RF tag or other optical sensor specific identifier to identify a specific optical sensor in question. The sensor ID 511 provides information identifying an optical sensor 300 that is location and/or sample specific depending on the particular sensor application. A sample specific optical sensor 300 can be so labeled via sensor ID 511 permitting electronic sub-system 520 to determine the location of the optical sensor 300 and, if desired, the specific sample which the individual optical sensor 300 is designed to detect. In an embodiment of the present invention, a plurality of optical sensors 300 can be placed in a remote field or facility, or combination thereof and the location and sample type determined via sensor ID 511. By including sensor ID 511 on a plurality of optical sensors 300 on or in the optical sub-system 510, a distributive network of optical sensors 300 can be obtained. Accordingly, a plurality of sensor ID 511 types are possible, including a barcode, radio frequency tag, color code, a label, electronic signature or memory stored identifier.

A specific type of optical sensor 300 is determined by the sensing surface 113, i.e., the coating on the optical window 140 of the optical sensor 300 (see FIG. 3 and FIGS. 4*a-c*). For example, the coating on the metal surface 145 of window 140 of optical sensor 300 may include SAM 401, hydrogel 402, or SAM+403 materials, or any combination of the three.

Figure 6A:
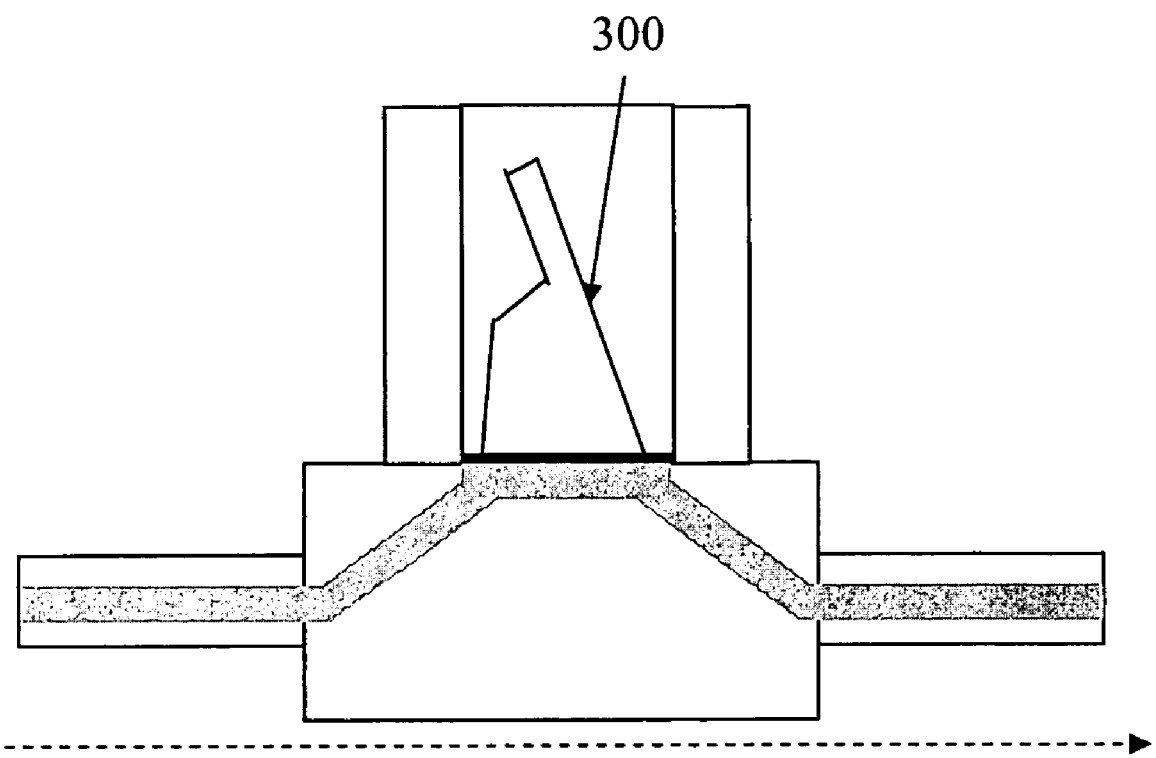
FIG. 6a illustrates an optical sensor coupled to an optical fluidic cell (OFC) according to an embodiment of the present invention.

Referring to FIG. 6*a*, in one embodiment of the present invention, an optical fluidic cell (OFC) 600 provides for the sampling interface 514 between the optical sensor 300 and the liquid under analysis. The OFC 600 materials of construction are compatible with acidic, basic, corrosive, solvents, ultrahigh purity, biological and biochemical applications. The OFC 600 may include a thermistor (not shown) to measure the liquid temperature. Temperature measurement may be input into a firmware algorithm as a temperature compensation feature.

Figure 6B:
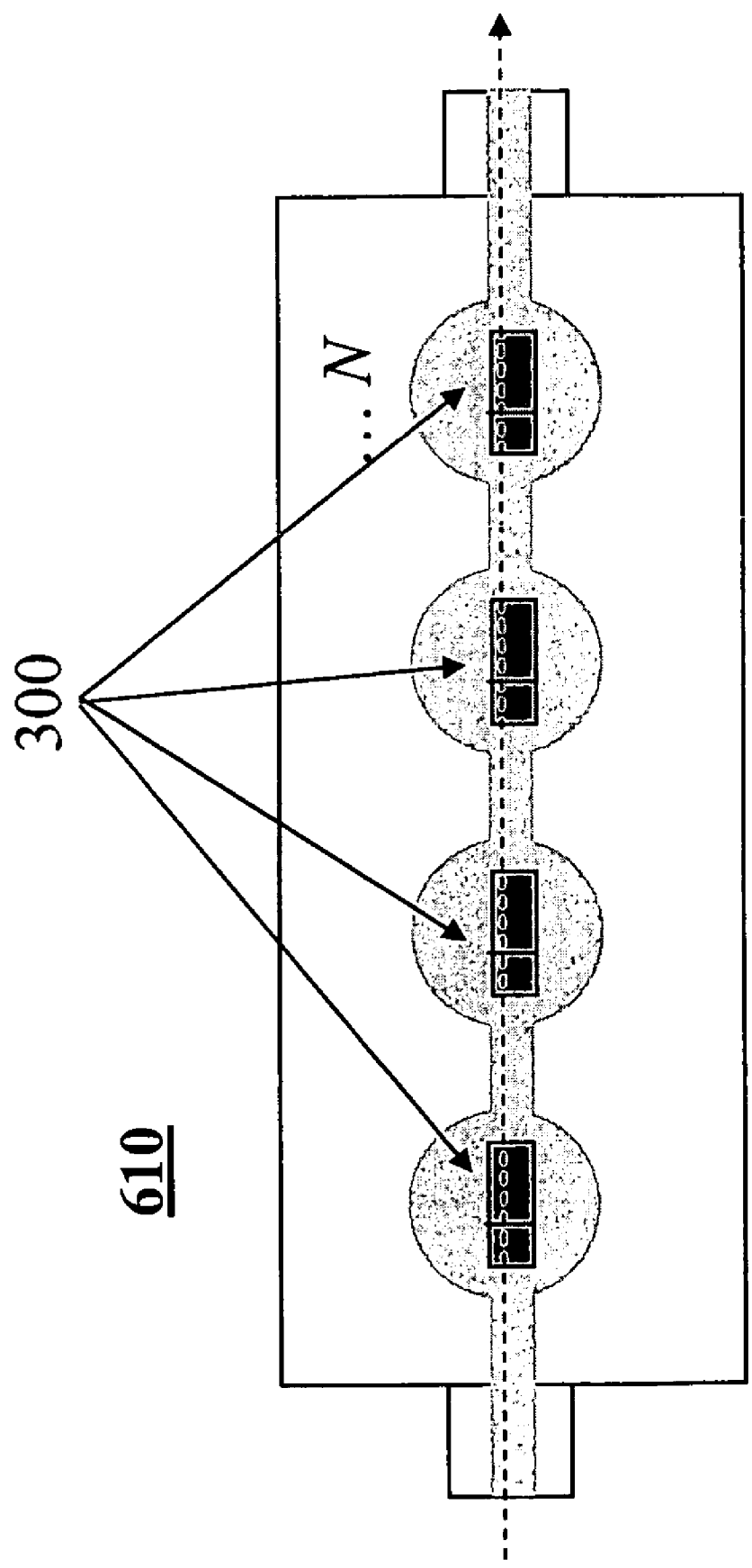
FIG. 6b illustrates an inline optical-fluidic manifold (OFM) including multiple optical sensors according to an embodiment of the present invention.

Referring to FIG. 6*b*, in another embodiment of the present invention, an optical fluidic manifold (OFM) 610 is shown. In this embodiment, 1, 2, 3 . . . N optical sensors 300 can be used simultaneously. By utilizing the OFM 610, each optical sensor 300 may be coated with a unique SAM 401, hydrogel 402, or SAM+403 material and therefore be used to analyze 1, 2, 3 . . . N unique metal ions.

Figure 6C:
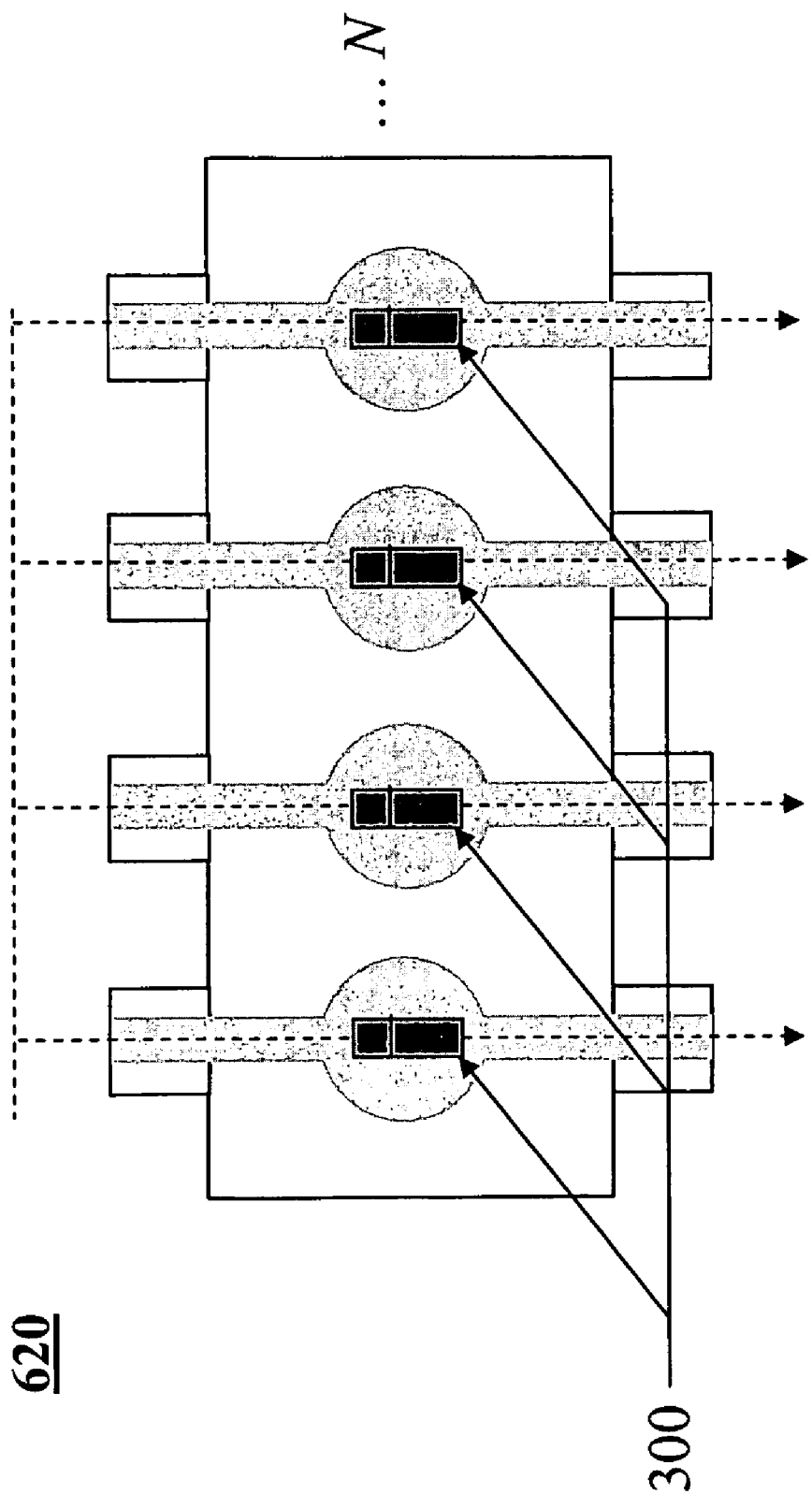
FIG. 6c illustrates a parallel inline optical-fluidic manifold (OFM) including multiple optical sensors according to an embodiment of the present invention.

Referring to FIG. 6*c*, in another embodiment, an OFM 620 may be modified to separate a single fluid stream into 1, 2, 3 . . . N parallel fluid streams.

Figure 6D:
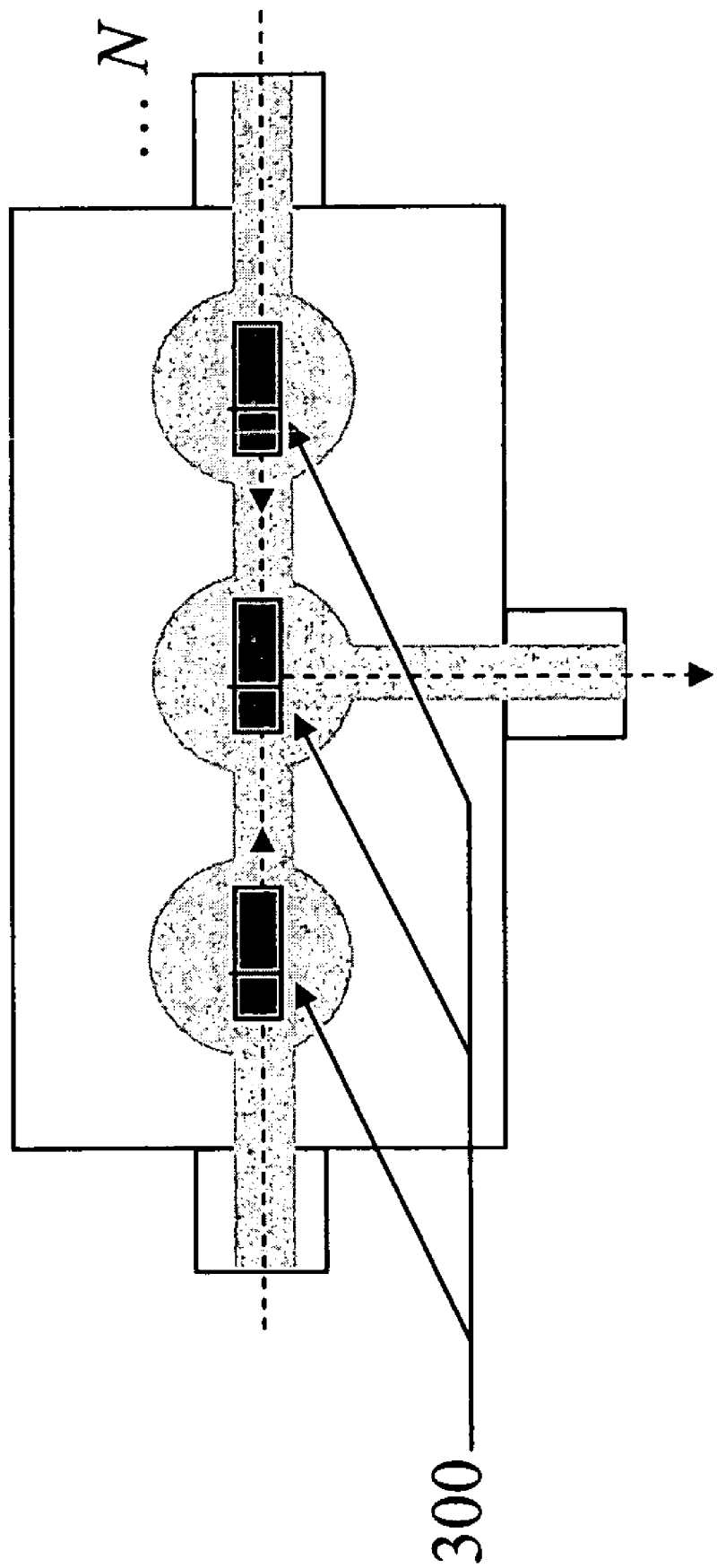
FIG. 6d illustrates a dual input single output optical-fluidic manifold (OFM) including multiple optical sensors according to an embodiment of the present invention.

Referring to FIG. 6*d*, in yet another embodiment 1, 2, 3 . . . N unique fluid streams can be input into an OFM 630.

This arrangement may provide measurement of several distinct metal ion species in a liquid simultaneously or measure several distinct metal ion species in several distinct liquids simultaneously.

Figure 6E:
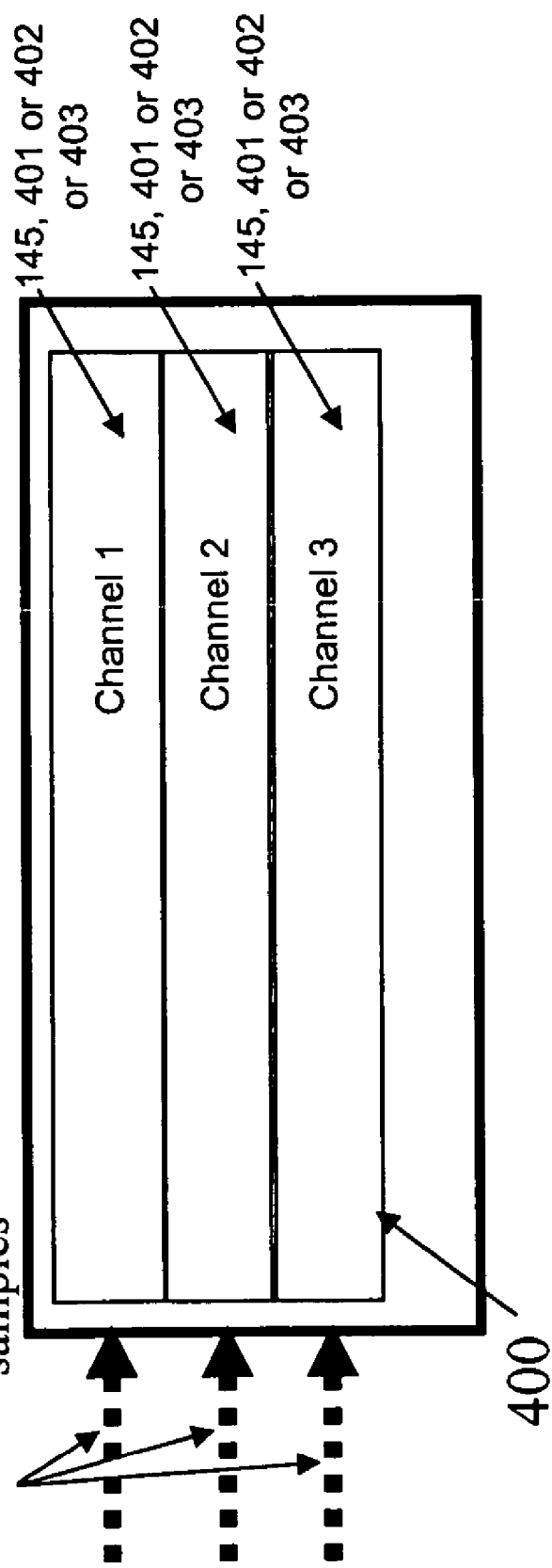
FIG. 6e illustrates a 1-3 channel micro-fluidic application according to an embodiment of the present invention.

Referring to FIG. 6e, in another embodiment, a multi-channel sensor 400 is used. This is accomplished by patterning an optical window 140 of the sensor 400 into three partitions. Each partition has a metal surface 145 and a coating 401, 402, 403 specific to the application and can be used for simultaneous and distinct in measurements. In the embodiment shown in FIG. 6e, a micro-fluidic OFC 640 is used. In this embodiment up to three fluid streams, either unique or redundant, flow over the sensor 400. In this embodiment up to three unique metal ions can be analyzed by using the three channel capability of a single multi-channel optical sensor 400.

All of these optical sensor 300, 400 embodiments of the present invention can be used in conjunction with an OFC or OFM to increase the number of distinct types of metal ions to be analyzed and the sensitivity and dynamic range of the analysis system.

A sampling interface 514 of the optical sub-system 510 depends primarily upon the type of OFC 600, 640 or OFM 610, 620, 630 used in the optical sub-system 510. Thus, direct contact, parallel flow, and static configurations are suitable OFC or OFM types. For example, the optical sensor 300 of the optical sub-system 510 can be manually introduced into the sample to make contact along a surface or other region of the optical sensor 300. Other sampling interfaces include fluidics, wherein the liquid sample is allowed to run over the optical sensor 300. In one use of the invention, the optical sub-system 510 is used in-situ and the electronic sub-system 520 is held at distance from the optical sub-system 510.

Referring to FIG. 5, communications interface 550 is provided to allow the optical sub-system 510 and electronic sub-system 520 to communicate via a wide array of communications formats. For example, communications interface 550 may comprise a plurality of signal paths or wires connecting the optical sub-system 510 to the electronic sub-system 520 which define physical signal pathways. Fiber optic cabling, twisted pair wiring, network, coax or other physical connections mediums may be used. Also, a communications protocol such as serial and/or parallel data transfers between the optical sub-system 510 and the electronic sub-system 520 may be employed. Likewise, communications interface 550 may take the form of a wireless communications system between the two sub-systems 510, 520 including radio frequency, infrared, satellite or other signal frequencies. Other communications interfaces 550 include point-to-point, on demand, secured transmissions or other custom communications protocol.

On the electronic sub-system 520 side, various functional features are provided and operationally coupled to each other. A source of power 521 is provided to activate and run the various active components of the electronic sub-system 520. Power source 521 can be solar, battery driven, alternating current, direct current, a generator or a remote power source, according to the invention.

An interface 522 gives the user input and functional control of the electronic sub-system 520 depending on the specific application of the analysis system 500. A keyboard, control pad, mouse, touch screen or other mechanical means of control and input may form part of the interface 522. Likewise, the interface 522 may be implemented as a remote control subassembly of the electronic sub-system 520 which is operationally coupled to the analysis system 500 for remote use and operation. In yet another contemplated embodiment, the interface 522 comprises a switch or button which the user activates in order to command sensor functions.

Software/firmware 523 may be maintained on the electronic sub-system 520 to control the various sensors functions and processes according to the specific sensor application. In one embodiment, the software/firmware 523 is controlled by the user interface 522 allowing the user to view and display data results via display 525 and/or otherwise manipulate the sample related data as obtained by the optical sub-system 510.

For example, the user can use interface 522, software/firmware 523, and display 525 to determine when the sample of interest is detected by the optical sub-system 510. The data can be manipulated, graphed or otherwise analyzed depending on software/firmware 523 features. A help system may also be included in the software/firmware 523 to assist the user with various analysis system 500 features. The software/firmware 523 may be used to store, retrieve or transmit data and/or commands to the sensor or a remote processing system according to the invention.

Also shown is a storage area 524 that can be a hard disk, floppy disk or other magnetic means of storage or a chip-based storage device such as DRAM, EEPROM, flash memory, ROM or other similar components. Storage area 524 provides a space where sample related data, test history, calibration information or other similar data can be stored.

A display 525 may be included and operationally coupled to the various components of the electronic sub-system 520. In an embodiment of the analysis system 500, display 525 comprises one or more LEDs which are actuated at times when the optical sub-system 510 detects the presence of the particular sample of interest. In other embodiments, display 525 comprises a liquid crystal display (LDC), a monitor or CRT which provides alpha-numeric output relating to the sample of interest. Other display 525 include hard copy, digital or analog signal outputs, audio alarm, synthetic voice, pager or projection among others.

Also shown is an electronic circuit 526 that includes a signal processor 527 in the electronic sub-system side 520 of the analysis system 500 which converts, processes, assembles and otherwise manipulates the data received from the optical sub-system 510. In one embodiment, the optical sub-system 510 generates a digital bitstream data output related to the sample of interest which is relayed via communications interface 550 to the electronic sub-system 520 and received by the signal processor 527 for further analysis. The data may be the output of an analog-digital converter which may be integrally molded on the optical sensor 300 or mounted externally.

In another embodiment, the output from the optical sub-system 510 is a modulated carrier that is transmitted to the signal processor 527 of the electronic circuit 526 via a wireless communications mode of communications interface 550.

For example, an RF transmitter can be incorporated in the optical sub-system 510 as part of communications interface 550 and used to modulate an airborne signal which is received by the communications interface 550 side of the electronic sub-system 520 and transferred to the signal processor 527 for demodulation and further analysis.

Figure 7:
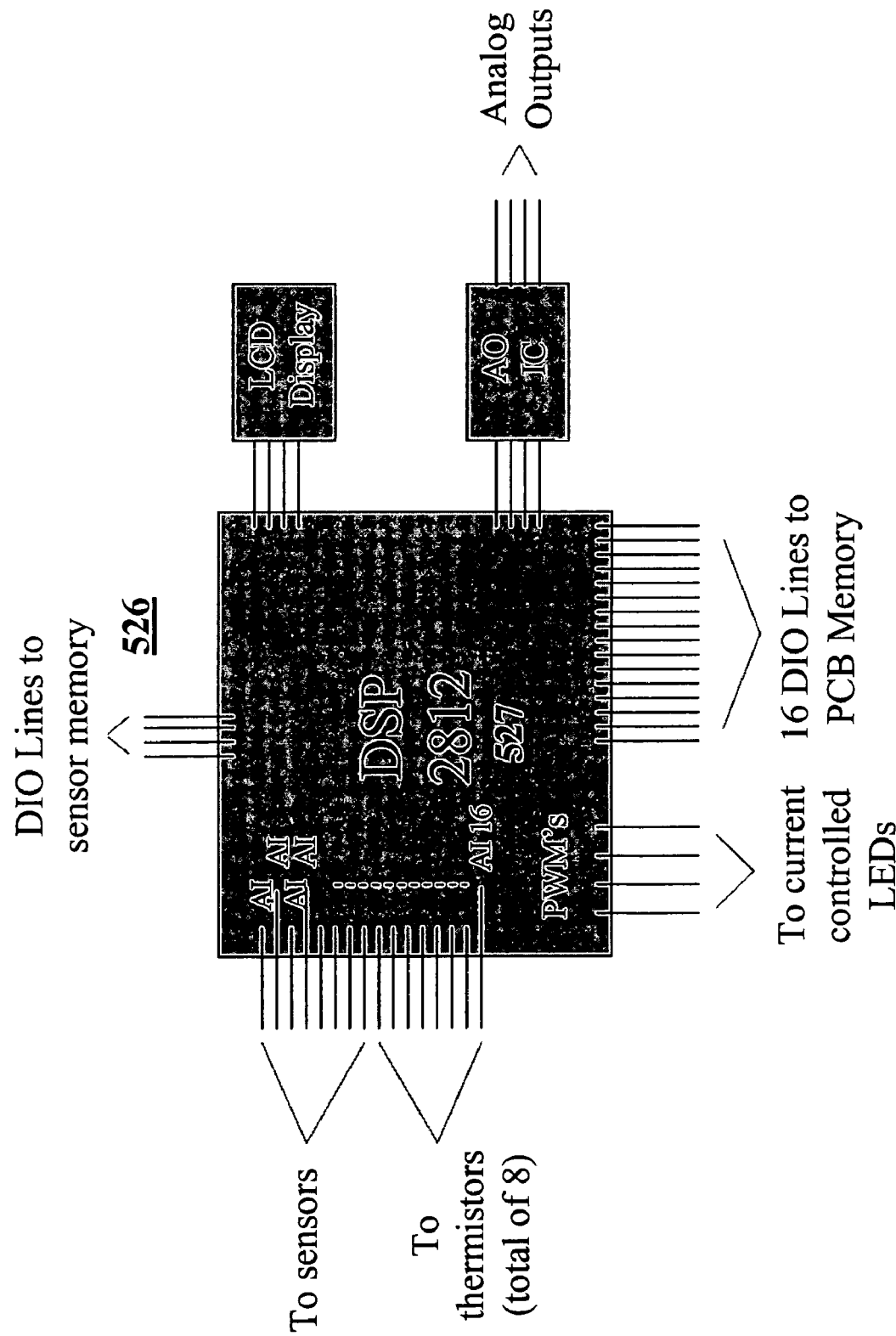
FIG. 7 illustrates DSP (digital signal processor) based electronic drive circuit according to an embodiment of the present invention.

FIG. 7 illustrates an electronic circuit 526 that incorporates a digital signal processor (DSP) as the signal processor 527. The DSP chip includes firmware and software inputs and data outputs and may be of a type readily available in the industry.

Figure 8A:
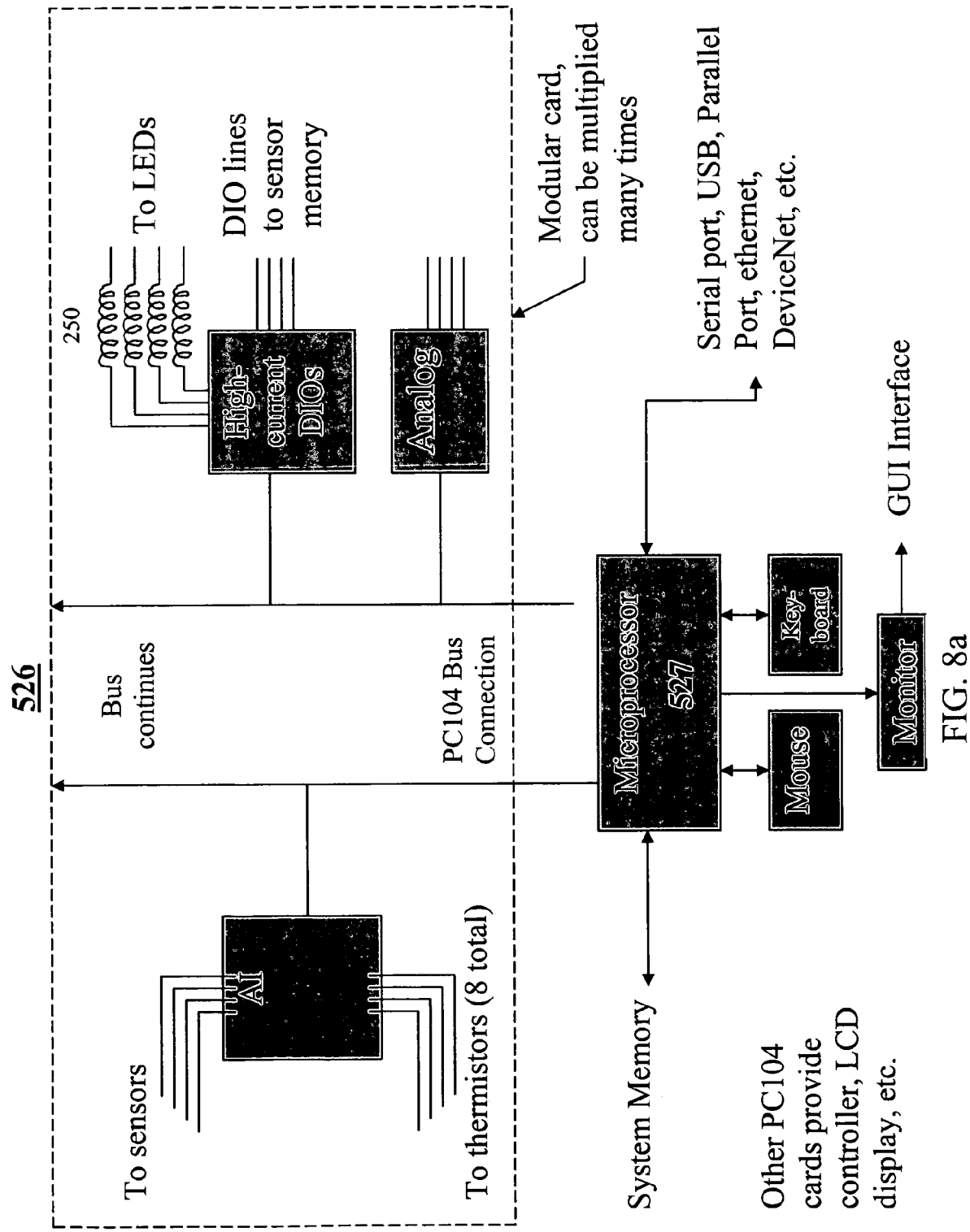
FIG. 8a illustrates a PC104 based electronic circuit according to an embodiment of the current invention.

FIG. 8 illustrates an electronic circuit 526 that includes a PC104-based embedded computing platform on a modular card that connects via a PC104 bus connection to a microprocessor that serves as the signal processor 527. Also a microcontroller, microprocessor or other high scale integrated circuit can be used as the signal processor 527 to analyze the incoming data from the optical sub-system 510. Other options include a data analyzer, calculator or application specific integrated circuit (ASIC).

Figure 8B:
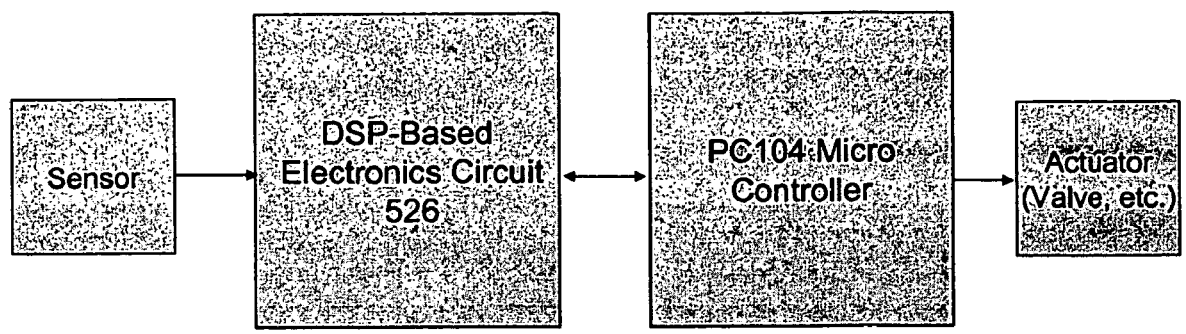
FIG. 8b illustrates a PC104 based electronic circuit interfaced to a PC 104 based microcontroller and an actuator according to an embodiment of the current invention.
Figure 8C:
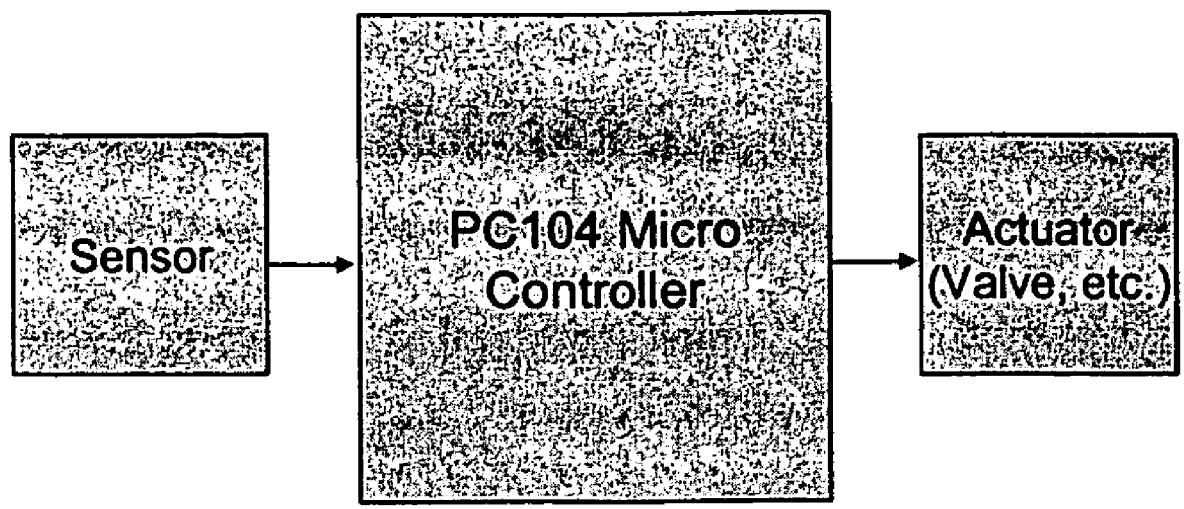
FIG. 8c illustrates a PC104 based electronic circuit used as a sensor electronic circuit and as a controller electronic circuit according to an embodiment of the current invention.

Referring to FIG. 8b, in another embodiment, the DSP-based electronic circuit 526 is interfaced to a PC104-based microcontroller, which is in turn interfaced to an actuator (valve, pump, etc.) for closed loop control of metal ion concentration, segregation and diversion of liquid streams, etc. Referring to FIG. 8c, in another embodiment, the PC104-based electronic circuit 526 is used both as the sensor electronic circuit and as the controller electronic circuit for closed-loop control applications.

Figure 9:
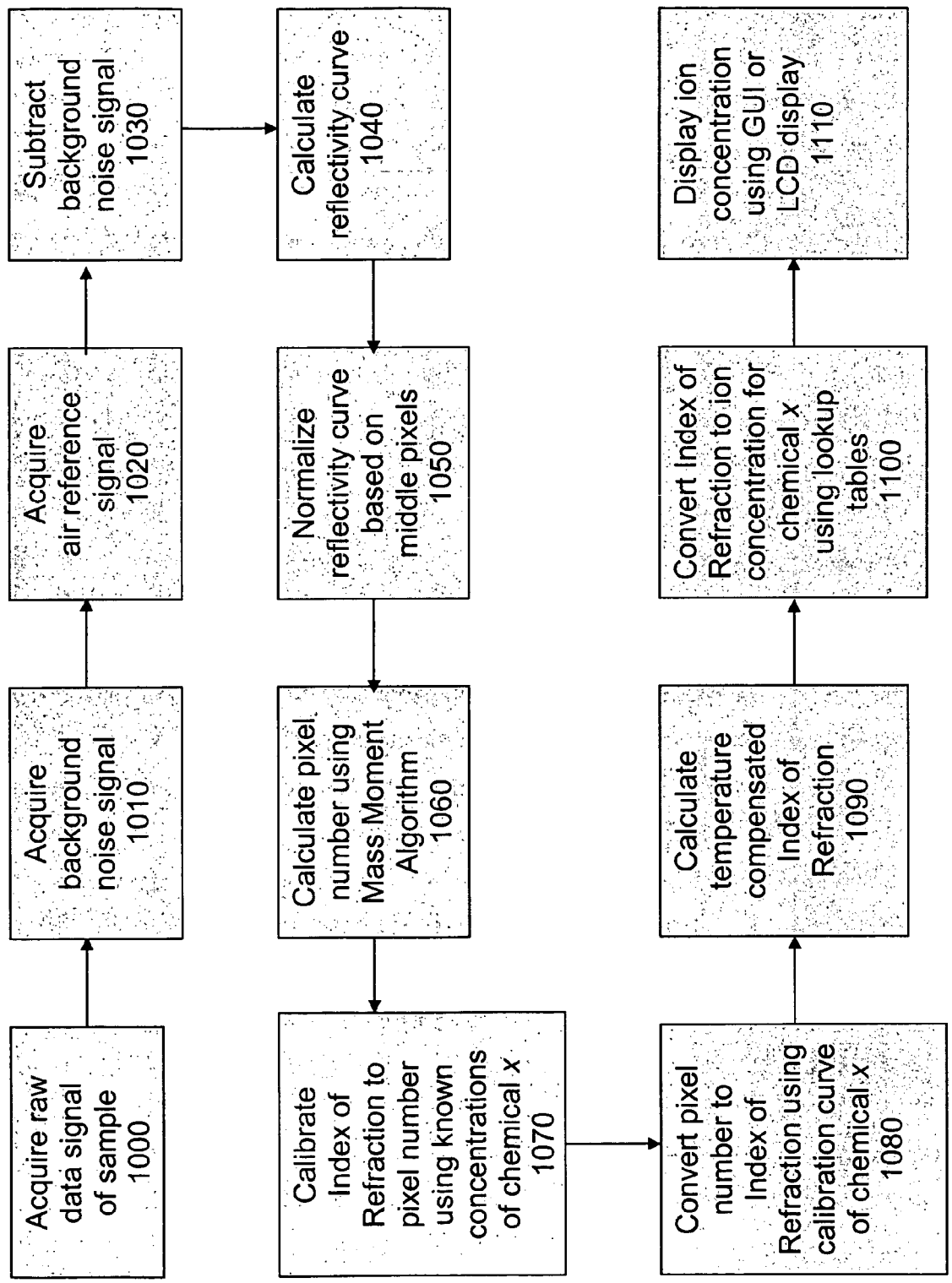
FIG. 9 illustrates a flow chart diagram of a method of measuring a metal ion concentration in a liquid using an algorithm according to an embodiment of the present invention.
Figure 10A:
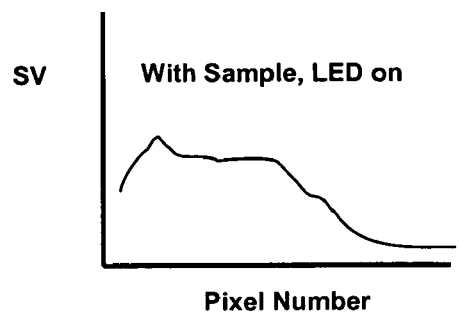
FIG. 10a illustrates a graph of a raw data signal obtained from a photodetector array according to an embodiment of the present invention.
Figure 10B:
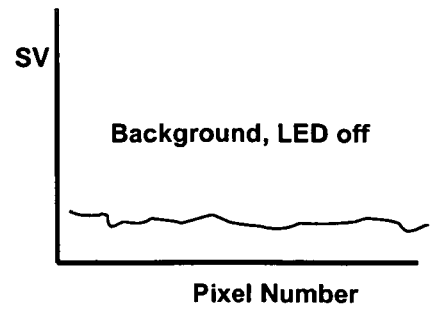
FIG. 10b illustrates a graph of a background noise signal obtained from a photodetector array with a light source off according to an embodiment of the present invention.
Figure 10C:
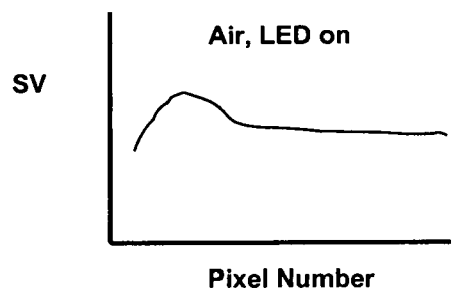
FIG. 10c illustrates a graph of an air reference signal obtained from a photodetector array according to an embodiment of the present invention.

FIG. 9 illustrates a flow chart diagram of a method of measuring a metal ion concentration of a known chemical X in a liquid using an algorithm according to an embodiment of the present invention. With reference to FIGS. 3, 5, 10a-e, 11a, 11b, 12, and 13a-d, the method will now be described. A signal processor 527 in the electronic circuit 526 of the electronic sub-system 520 data acquires 1000 a raw data signal by reading out the pixel data from a photodetector array 110 in the optical sensor 300 of the optical sub-system 510 in contact with the test sample (see FIG. 10a). The signal processor 527 acquires 1010 a background noise signal from the photodetector array 110 by turning off the light source 120 in the optical sensor 300 and reading out the pixel data (see FIG. 10b). The signal processor 527 acquires 1020 an air reference signal from the photodetector array 110 by making a measurement with air as the sample in contact with the optical sensor 300 and reading out the pixel data (see FIG. 10c). The signal processor 527 subtracts 1030 the background noise signal from the raw data signal and subtracts 1030 the background noise signal from the air reference signal. The signal processor 527 calculates 1040 a reflectivity curve by dividing the result of subtraction of the background noise signal from the raw data signal by the result of the subtraction of the background noise signal from the air reference signal according to the following equation (see FIG. 10d):

(Raw data signal−Background noise signal)/(Air reference signal−Background noise signal)

Figure 10D:
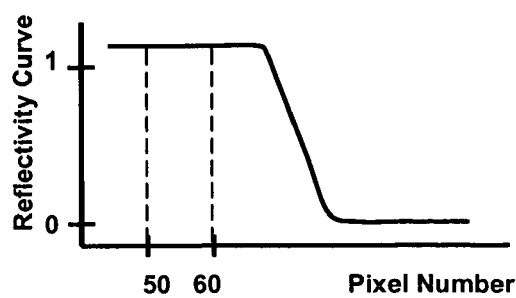
FIG. 10d illustrates a graph of a reflectivity curve according to an embodiment of the present invention.
Figure 10E:
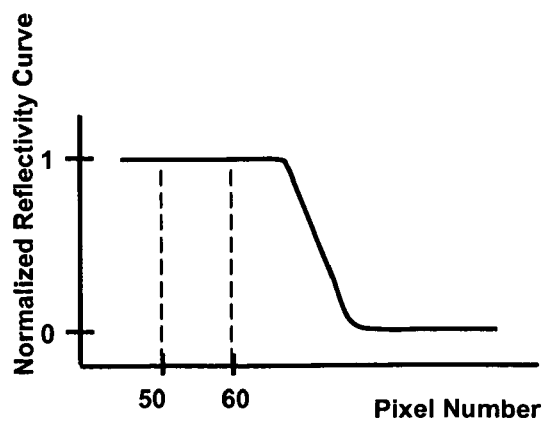
FIG. 10e illustrates a graph of a normalized reflectivity curve according to an embodiment of the present invention.

The signal processor 527 normalizes 1050 the reflectivity curve by dividing the reflectivity curve by the average value of the intensity of a set of pixels located in the middle portion of the peak area of the reflectivity curve (see FIG. 10d and FIG. 10e).

The signal processor 527 calculates 1060 a pixel number correlating to a critical angle at which SPR occurs using the normalized reflectivity curve and a Mass Moment Algorithm based on the following equation:

$$MM = \frac{\sum_{i=a}^{b} i|S_i - T_h|}{\sum_{i=a}^{b} |S_i - T_h|}$$

Figure 11A:
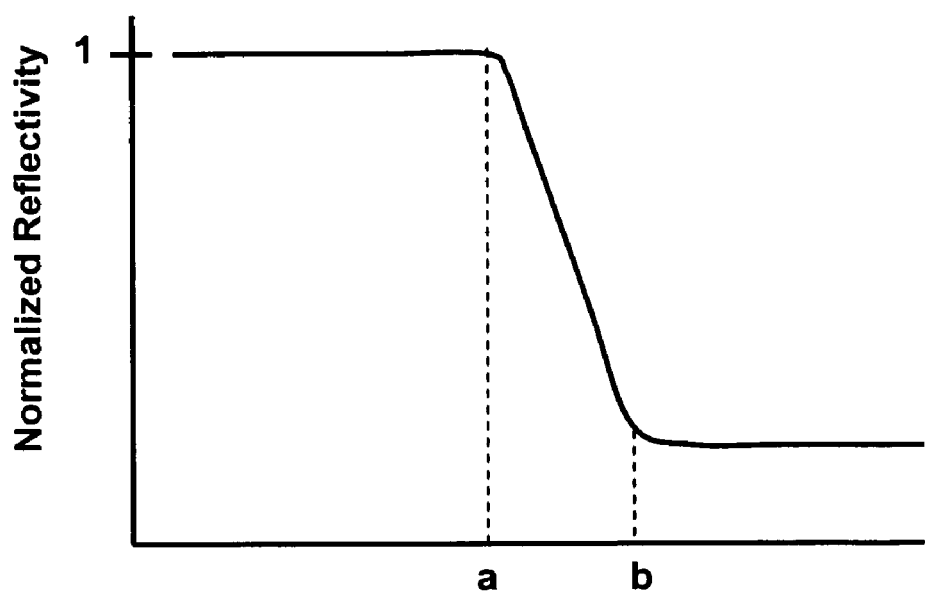
FIG. 11a illustrates a graph of a normalized reflectivity curve highlighting the slope section according to an embodiment of the present invention.
Figure 11B:
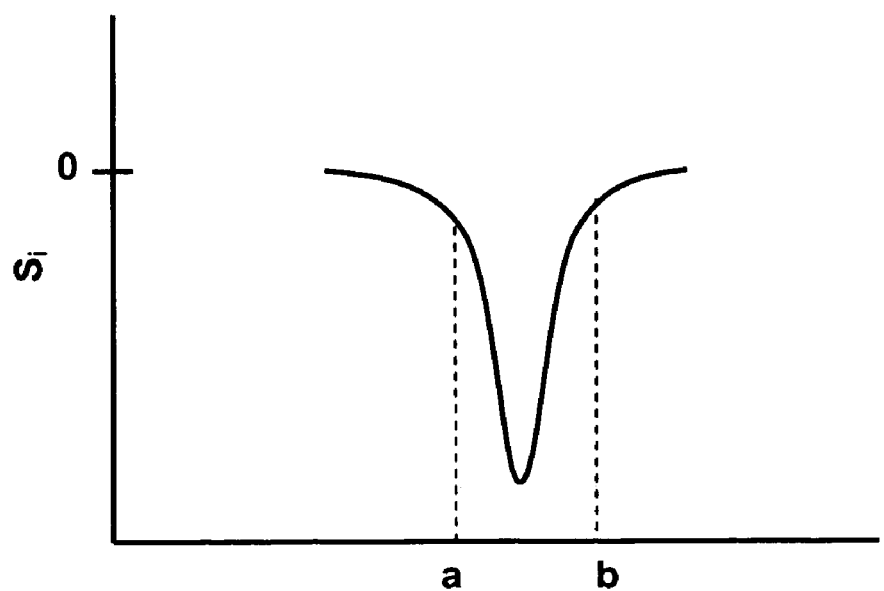
FIG. 11b illustrates a graph obtained using a mass moment algorithm according to an embodiment of the present invention.
Figure 12:
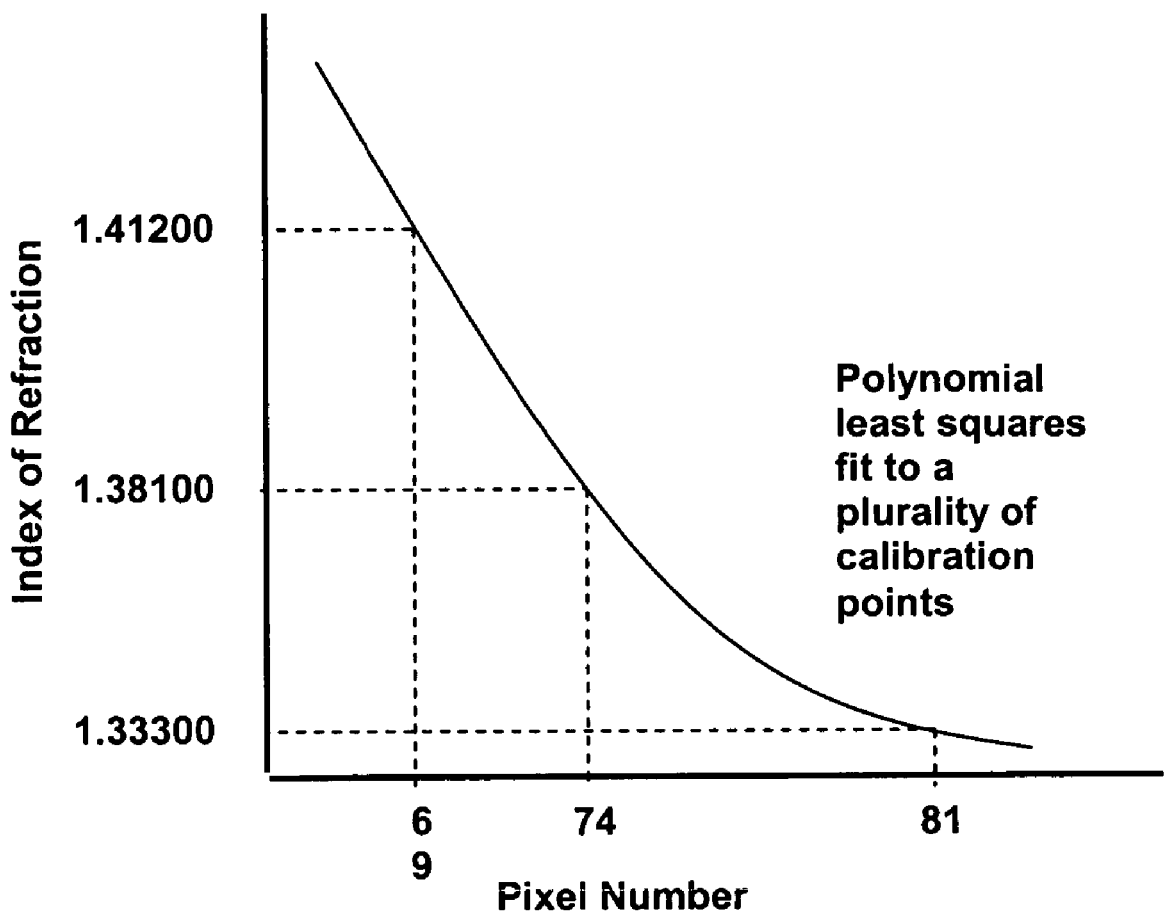
FIG. 12 illustrates a graph of a calibration curve according to an embodiment of the present invention.
Figure 13A:
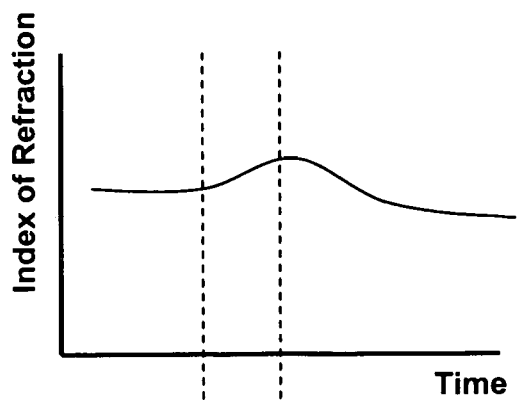
FIG. 13a illustrates a graph of a measured index of refraction as a function of time according to an embodiment of the present invention.
Figure 13B:
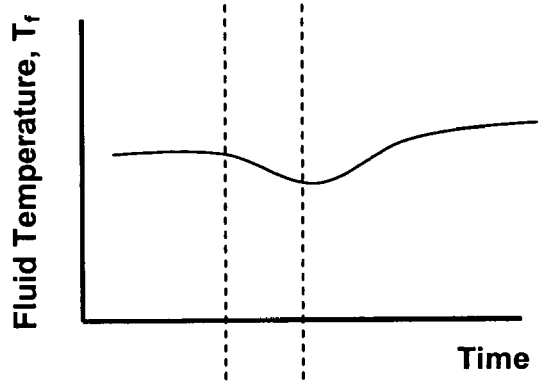
FIG. 13b illustrates a graph of a measured fluid temperature as a function of time according to an embodiment of the present invention.
Figure 13D:
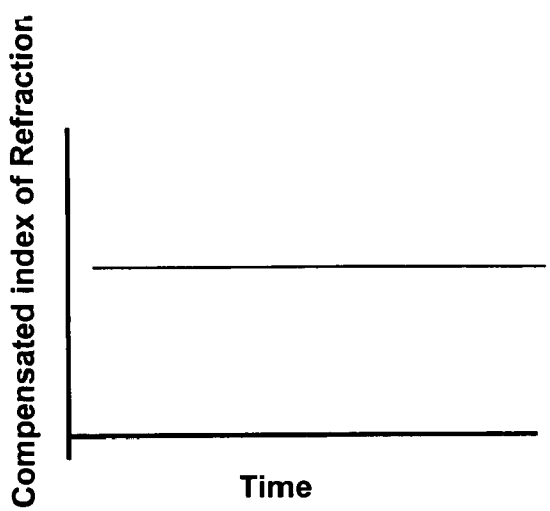
FIG. 13d illustrates a graph of a compensated index of refraction as a function of time according to an embodiment of the present invention.
Figure 13C:
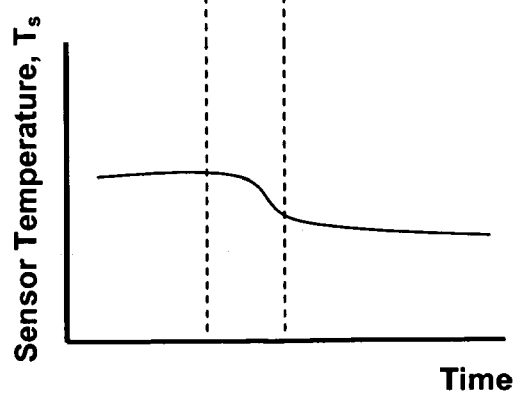
FIG. 13c illustrates a graph of a measured sensor temperature as a function of time according to an embodiment of the present invention.

Referring to FIG. 11a and FIG. 11b, "a" and "b" indicate angles where $S_i$ crosses $T_h$. Calculating the "mass moment" at approximately the reference value, $T_h = -0.03$. $T_h$ is the threshold voltage and $S_i$ is the voltage at the $i^{th}$ pixel and i is the pixel number.

A variety of other Algorithms may be used as well, including an nth degree polynomial approximation of the shadow line, intersected with a threshold value.

The signal processor 527 calibrates 1070 the index of refraction to pixel number using known concentrations of the known sample under test, chemical X. A polynomial least squares fit to a plurality of calibration points is used to generate the calibration curve of known chemical X (see FIG. 12). The signal processor 527 converts 1080 the calculated pixel number to an index of refraction using the calibration curve of known chemical X (see FIG. 12).

The signal processor 527 calculates 1090 a temperature compensated index of refraction using a sensor temperature measured by the temperature sensor 125 in the optical sensor 300, a known fluid temperature measured by a thermistor(s) in the OFC or OFM (see FIG. 6a-e), the measured index of refraction as a function of time, and the following equation (see FIG. 13a-d):

compRI=RI−$a(T_f-20)+b(T_s-20)$ $a \approx 1.3e-04$ $b \approx 0.3e-04$

Where compRI is the temperature compensated refractive index, RI is the measured refractive index, $T_f$ is the known temperature of the fluid, and $T_s$ is the temperature of the sensor.

The signal processor 527 converts 1100 the temperature compensated index of refraction to an ion concentration for chemical X in solution using lookup tables of known chemical X. The signal processor 527 displays 1110 the calculated ion concentration using, for example, display 525, a graphical user interface (GUI) or an LCD display.

An analysis system 500 has been defined that incorporates miniaturized sensor technology having fixed optics inside a rigid, self-contained sensor platform or housing. The analysis system 500 combines an assortment of communications interface 550 which permits the integrated miniaturized optical sensor 300 of optical sub-system 510 to be placed at or near the sample of interest without interference from field personnel.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An optical sensor for selectively measuring a metal ion concentration in a sample of interest, comprising:
   a substrate having an interior surface and an exterior surface;
   an optical housing coupled to said substrate and having a sensing surface that forms the interface between said optical sensor and the sample of interest;
   a surface plasmon resonance (SPR) layer in contact with said sensing surface;

a self assembled monolayer (SAM) in contact with said SPR layer for selectively binding metal ions;

a photodetector array coupled to said interior surface of said substrate and enclosed in said optical housing; and a light source coupled to said interior surface of said substrate adjacent said photodetector array, said light source enclosed in said optical housing and spatially arranged inside said optical housing to emit light in the direction of said sensing surface, wherein a portion of said light is internally reflected off said sensing surface as a function of the concentration of metal ions bound to said SAM layer, said portion of said light being internally reflected to said photodetector array to determine the intensity thereof.

2. The optical sensor as recited in claim 1, wherein selective binding of metal ions to said SAM occurs via a mechanism selected from the group consisting of a physisorption (van der Waals, Coulombic, electrostatic interactions), a chemisorption (chemical bond), a geometrical bonding, and a spatial bonding.

3. The optical sensor as recited in claim 1, wherein the SAM includes a plurality of head groups for selective binding of metal ions.

4. The optical sensor as recited in claim 1, wherein said housing is composed of a material having a higher index of refraction than the sample of interest.

5. The optical sensor as recited in claim 1, wherein said housing is composed of light transmissive epoxy material.

6. The optical sensor as recited in claim 1, wherein said housing has a substantially pyramidal shape.

7. The optical sensor as recited in claim 1, wherein said housing has a substantially trapezoidal shape.

8. The optical sensor as recited in claim 1, wherein said photodetector array is a solid state linear photodiode array.

9. The optical sensor as recited in claim 1, further including a light reflective surface spatially inside said housing to receive light from said light source and direct it towards said photodetector array.

10. The optical sensor as recited in claim 7, wherein said light reflective surface is a planar surface.

11. The optical sensor as recited in claim 7, wherein said light reflective surface is a concave surface.

12. The optical sensor as recited in claim 1, wherein said sensing surface includes an optical window made from a material selected from the group consisting of quartz, sapphire, and glass.

13. The optical sensor as recited in claim 1, further including a signal processing unit coupled to said interior surface of said substrate and electronically connected to said photodetector array.

14. The optical sensor as recited in claim 13, wherein the signal processing unit is preprogrammable.

15. The optical sensor as recited in claim 1, further including a plurality of conductive leads coupled to said exterior surface of said substrate and forming conductive pathways to said photodetector array.

16. The optical sensor as recited in claim 1, further including a temperature sensor embedded in said housing.

17. The optical sensor as recited in claim 16, wherein said temperature sensor is disposed in close proximity to said sensing surface of said housing.

18. An optical sensor for selectively measuring a metal ion concentration in a sample of interest, comprising:

a substrate having an interior surface and an exterior surface;

an optical housing coupled to said substrate and having a sensing surface that forms the interface between said optical sensor and the sample of interest;

a surface plasmon resonance (SPR) layer in contact with said sensing surface;

a hydrogel in contact with said SPR layer for selectively binding metal ions;

a photodetector array coupled to said interior surface of said substrate and enclosed in said optical housing; and a light source coupled to said interior surface of said substrate adjacent said photodetector array, said light source enclosed in said optical housing and spatially arranged inside said optical housing to emit light in the direction of said sensing surface, wherein a portion of said light is internally reflected off said sensing surface as a function of the concentration of metal ions bound to said hydrogel, said portion of said light being internally reflected to said photodetector array to determine the intensity thereof.

19. The optical sensor as recited in claim 18, wherein selectively binding of metal ions to said hydrogel occurs via a mechanism selected from the group consisting of a physisorption (van der Waals, Coulombic, electrostatic interactions), a chemisorption (chemical bond), a geometrical bonding, and a spatial bonding.

20. The optical sensor as recited in claim 18, wherein said housing is composed of a material having a higher index of refraction than the sample of interest.

21. The optical sensor as recited in claim 18, wherein said housing is composed of light transmissive epoxy material.

22. The optical sensor as recited in claim 18, wherein said housing has a substantially pyramidal shape.

23. The optical sensor as recited in claim 18, wherein said housing has a substantially trapezoidal shape.

24. The optical sensor as recited in claim 18, wherein said photodetector array is a solid state linear photodiode array.

25. The optical sensor as recited in claim 18, further including a light reflective surface spatially inside said housing to receive light from said light source and direct it towards said photodetector array.

26. The optical sensor as recited in claim 25, wherein said light reflective surface is a planar surface.

27. The optical sensor as recited in claim 25, wherein said light reflective surface is a concave surface.

28. The optical sensor as recited in claim 18, wherein said sensing surface includes an optical window made from a material selected from the group consisting of quartz, sapphire, and glass.

29. The optical sensor as recited in claim 18, further including a signal processing unit coupled to said interior surface of said substrate and electronically connected to said photodetector array.

30. The optical sensor as recited in claim 29, wherein the signal processing unit is preprogrammable.

31. The optical sensor as recited in claim 18, further including a plurality of conductive leads coupled to said exterior surface of said substrate and forming conductive pathways to said photodetector array.

32. The optical sensor as recited in claim 18, further including a temperature sensor embedded in said housing.

33. The optical sensor as recited in claim 32, wherein said temperature sensor is disposed in close proximity to said sensing surface of said housing.

34. An optical sensor for measuring a metal ion concentration in a sample of interest using the positional intensity of incident light reflected from an interface between the optical sensor and the sample of interest, the optical sensor comprising:

a substrate having an interior surface and an exterior surface;

an optical housing coupled to said substrate and having a sensing surface including an optical window that forms the interface between said optical sensor and the sample of interest, said optical housing also having a first surface, the first surface forming a front face of a reflective mirror, the reflective mirror spatially arranged to receive light from said sensing surface and direct it towards said interior surface, said optical housing made of a single piece of material with a refractive index selected for its known relation to a refractive index of said sample of interest;

a surface plasmon resonance (SPR) layer in contact with said sensing surface;

a self assembled monolayer (SAM) including a molecular adhesion layer in contact with said SPR layer, wherein the molecular adhesion layer selectively binds metal ions;

a photodetector array coupled to said interior surface of said substrate and enclosed in said optical housing to receive light from said reflective mirror; and a light source coupled to said interior surface of said substrate adjacent said photodetector array, said light source enclosed in said optical housing and spatially arranged inside said optical housing to emit light in the direction of said sensing surface, wherein a portion of said light is internally reflected off said sensing surface as a function of the concentration of metal ions bound to said molecular adhesion layer, said portion of said light being internally reflected to said reflective mirror and then to said photodetector array to determine the intensity thereof.

35. The optical sensor as recited in claim 34, wherein selective binding of metal ions to said molecular adhesion layer occurs via a mechanism selected from the group consisting of a physisorption (van der Waals, Coulombic, electrostatic interactions), a chemisorption (chemical bond), a geometrical bonding, and a spatial bonding.

36. The optical sensor as recited in claim 34, wherein the molecular adhesion layer includes a plurality of head groups for selective binding of metal ions.

37. The optical sensor as recited in claim 34, wherein said photodetector array is a linear photodiode array.

38. The optical sensor as recited in claim 34, wherein said housing has an optical geometry that allows light from said light source to strike said sensing surface and reflect off said sensing surface to strike said photodetector array.

39. The optical sensor as recited in claim 34, wherein said housing is composed of a medium with a higher index of refraction as compared to the sample of interest.

40. The optical sensor as recited in claim 34, wherein said first surface is a planar surface.

41. The optical sensor as recited in claim 34, wherein said optical window is made from a material selected from the group consisting of quartz, sapphire, and glass.

42. A critical angle sensor comprising:

a substrate having an interior surface with at least one light emitting diode and a photodetector array coupled thereto and a exterior surface with a plurality of signal pins extending therefrom; and a unitary light transmissive optical housing made from a single piece of material coupled to said substrate in an encapsulating manner over said interior surface, said housing integrally encapsulating said at least one light emitting diode and said photodetector array, said housing having a first surface and a sensing surface, wherein a surface plasmon resonance (SPR) layer is in contact with said sensing surface and a self assembled monolayer (SAM) including a molecular adhesion layer is in contact with said SPR layer, the molecular adhesion layer selectively binds metal ions, said first surface forming the front face of a reflective mirror, the reflective mirror predisposed to receive light from said sensing surface and direct it towards said photodetector array, said sensing surface predisposed to receive light from said light emitting diode, and wherein a portion of said received light is internally reflected off said sensing surface as a function of the concentration of metal ions bound to said molecular adhesion layer, said portion of said light being internally reflected to said reflective mirror and then to said photodetector array to determine the intensity thereof.

43. The critical angle sensor as recited in claim 42, further including a signal processing unit coupled to said interior surface of said substrate and electronically interconnected between said photodetector array and said plurality of signal pins.

44. The critical angle sensor as recited in claim 43, wherein the signal processing unit is pre-programmable.

45. The critical angle sensor as recited in claim 44, wherein said photodetector array is a solid state linear photodiode array.

46. The critical angle sensor as recited in claim 42, further including a temperature sensor coupled to said interior surface of said substrate and embedded in said housing.

47. The critical angle sensor as recited in claim 42, wherein selective binding of metal ions to said molecular adhesion layer occurs via a mechanism selected from the group consisting of a physisorption (van der Waals, Coulombic, electrostatic interactions), a chemisorption (chemical bond), a geometrical bonding, and a spatial bonding.

48. The critical angle sensor as recited in claim 42, wherein the molecular adhesion layer includes a plurality of head groups for selective binding of metal ions.

49. A method of measuring a metal ion concentration in a liquid using an optical sensor comprising:

acquiring a raw data signal by reading out pixel data from an optical detector in the optical sensor in contact with a known sample under test;

acquiring a background noise signal from the photodetector array;

acquiring an air reference signal from the photodetector array;

subtracting the background noise signal from the raw data signal and subtracting the background noise signal from the air reference signal;

calculating a reflectivity curve;

normalizing the reflectivity curve;

calculating a pixel number correlating to a critical angle at which surface plasmon resonance (SPR) occurs;

calibrating an index of refraction to a pixel number by generating a calibration curve of the known sample under test;

converting the calculated pixel number to an index of refraction using the calibration curve;

calculating a temperature compensated index of refraction;

converting the temperature compensated index of refraction to an ion concentration for the known sample under test; and displaying the calculated ion concentration using a display.

50. A method according to claim 49, wherein the optical detector includes a photodetector array.

51. A method according to claim 49, wherein acquiring a background noise signal from the photodetector array includes turning off a light source in the optical sensor and reading out the pixel data.

52. A method according to claim 49, wherein acquiring an air reference signal from the optical detector includes making a measurement with air as a sample in contact with the optical sensor and reading out the pixel data.

53. A method according to claim 49, wherein calculating a reflectivity curve includes dividing a result of subtraction of the background noise signal from the raw data signal by a result of a subtraction of the background noise signal from the air reference signal.

54. A method according to claim 49, wherein normalizing the reflectivity curve includes dividing the reflectivity curve by an average value of an intensity of a set of pixels located in a middle portion of a peak area of the reflectivity curve.

55. A method according to claim 49, wherein calculating a pixel number correlating to a critical angle at which surface plasmon resonance (SPR) occurs includes using the normalized reflectivity curve and a Mass Moment Algorithm.

56. A method according to claim 49, wherein calculating a pixel number correlating to a critical angle at which surface plasmon resonance (SPR) occurs includes using an nth degree polynomial approximation of the shadow line, intersected with a threshold value.

57. A method according to claim 49, wherein calibrating an index of refraction to a pixel number includes using known concentrations of the known sample under test.

58. A method according to claim 49, wherein converting the calculated pixel number to an index of refraction includes using the calibration curve of the known sample under test.

59. A method according to claim 49, wherein calculating a temperature compensated index of refraction includes using a sensor temperature measured by a temperature sensor in the optical sensor, a known fluid temperature measured by a thermistor in an optical fluidic cell (OFC) or optical fluidic manifold (OFM), and the measured index of refraction as a function of time.

60. A method according to claim 49, wherein converting the temperature compensated index of refraction to an ion concentration for the known sample under test in solution includes using lookup tables of the known sample under test.

61. A method according to claim 49, wherein displaying the calculated ion concentration using a display includes using a graphical user interface (GUI) or an LCD display.

62. A method according to claim 49, wherein generating the calibration curve includes using a polynomial least squares fit to a plurality of calibration points.

* * * * *